(12) United States Patent
Liu et al.

(10) Patent No.: US 8,148,056 B2
(45) Date of Patent: Apr. 3, 2012

(54) METHODS OF IDENTIFYING MODULATORS OF GPR81 RECEPTORS

(75) Inventors: Changlu Liu, San Diego, CA (US); Timothy W. Lovenberg, San Diego, CA (US); Jiejun Wu, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 1037 days.

(21) Appl. No.: 12/080,448

(22) Filed: Apr. 1, 2008

(65) Prior Publication Data

US 2011/0104711 A1   May 5, 2011

Related U.S. Application Data

(63) Continuation-in-part of application No. PCT/US2007/021924, filed on Oct. 11, 2007.

(60) Provisional application No. 60/851,681, filed on Oct. 13, 2006.

(51) Int. Cl.
*C12Q 1/00* (2006.01)
*G01N 33/53* (2006.01)

(52) U.S. Cl. ............................. 435/4; 435/7.1

(58) Field of Classification Search ........................ None
See application file for complete search history.

(56) References Cited

U.S. PATENT DOCUMENTS

| | | | |
|---|---|---|---|
| 5,223,409 | A | 6/1993 | Ladner et al. |
| 5,571,698 | A | 11/1996 | Ladner et al. |
| 2003/0077734 | A1 | 4/2003 | Ye et al. |
| 2003/0171541 | A1 | 9/2003 | Elliott et al. |
| 2004/0142377 | A1 | 7/2004 | Unett et al. |
| 2005/0069976 | A1 | 3/2005 | Lind et al. |
| 2005/0154029 | A1 | 7/2005 | Unett et al. |

FOREIGN PATENT DOCUMENTS

| | | |
|---|---|---|
| WO | WO 01/36471 | 5/2001 |
| WO | WO 01/77320 | 10/2001 |
| WO | WO 01/98330 | 12/2001 |
| WO | WO 02/00719 | 1/2002 |
| WO | WO 03/002604 | 1/2003 |

OTHER PUBLICATIONS

Andriamampandry et al., "Cloning and characterization of a rat brain receptor that binds the endogenous neuromodulator gamma-hydroxybutyrate", *The FASEB J*, 2003, vol. 17, pp. 1691-1693.
Bernasconi et al., "Gamma-hydroxybutyric acid: an endogenous neuromodulator with abuse potential?", *TiPS*, 1999, vol. 20, pp. 135-141.
Civelli et al., "Novel neurotransmitters as natural ligands of orphan G-protein-coupled receptors", *Trends Neurosci.*, 2001, vol. 24(4), pp. 230-237.
Clark et al., "Dichloroacetate inhibits glycolysis and augments insulin-stimulated glycogen synthesis in rat muscle", *J Clin Invest.*, 1987, vol. 79, pp. 588-594.
Cull et al., "Screening for receptor ligands using large libraries of peptides linked to the C terminus of the lac repressor", *Proc Natl Acad Sci. USA*, 1992, vol. 89, pp. 1865-1869.
Fodor et al., "Multiplexed biochemical assays with biological chips", *Nature*, 1993, vol. 364, pp. 555-556.
Gonzalez et al., "Gamma hydroxy butyrate abuse and dependency", *J Psychopharmacol.*, 2005, vol. 19(2), pp. 195-204.
Hampson et al., "Probing the ligand-binding domain of the mGluR4 subtype of metabotropic glutamate receptor", *J Biol Chem.*, 1999, vol. 274(47), pp. 33488-33495.
Houghten et al., "The use of synthetic peptide combinatorial libraries for the identification of bioactive peptides", *Biotechniques*, 1992, vol. 13(3), pp. 412-421.
Howard et al., "Orphan G-protein-coupled receptors and natural ligand discovery", *Trends Pharmacol Sci.*, 2001, vol. 22(3), pp. 132-140.
Lam et al., "A new type of synthetic peptide library for identifying ligand-binding activity", *Nature*, 1991, vol. 354, pp. 82-84.
Lam, "Application of combinatorial library methods in cancer research and drug discovery", *Anticancer Drug Des.*, 1997, vol. 12, pp. 145-167.
Lam et al., "Regulation of blood glucose by hypothalamic pyruvate metabolism", *Science*, 2005, vol. 309, pp. 943-947.
Lee et al., "Discovery and mapping of ten novel G protein-coupled receptor genes", *Gene*, 2001, vol. 275, pp. 83-91.
Liu et al., "Relaxin-3/insulin-like peptide 5 chimeric peptide, a selective ligand for G protein-coupled receptor (GPCR)135 and GPCR142 over leucine-rich repeat-containing G protein-coupled receptor 7", *Mol Pharmacol.*, 2005, vol. 67(1), pp. 231-240.
Liu et al., "Comparison of human, mouse, rat, and guinea pig histamine H4 receptors reveals substantial pharmacological species variation", *J Pharmacol Exp Ther.*, 2001, vol. 299(1), pp. 121-130.
Liu et al., "Identification of relaxin-3/INSL7 as an endogenous ligand for the orphan G-protein-coupled receptor GPCR135", *J Biol Chem.*, 2003, vol. 278(50), pp. 50754-50764.
Liu et al., "INSL5 is a high affinity specific agonist for GPCR142 (GPR100)", *J Biol Chem.*, 2005, vol. 280(1), pp. 292-300.
Maitre, "The gamma-hydroxybutyrate signalling system in brain: organization and functional implications", *Prog Neurobiol.*, 1997, vol. 51, pp. 337-361.
Mao et al., "T lymphocyte activation gene identification by coregulated expression on DNA microarrays", *Genomics*, 2004, vol. 83, pp. 989-999.
Montminy et al., "Regulation of cAMP-inducible genes by CREB", *TINS.*, 1990, vol. 13(5), pp. 184-188.
O'Hara et al., "The ligand-binding domain in metabotropic glutamate receptors is related to bacterial periplasmic binding proteins", *Neuron*, 1993, vol. 11, pp. 41-52.
Ribes et al., "Evidence for a role of exogenous or endogenous hyperlactatemia in insulin secretion in the dog", *J Physiol.* Paris, 1979, vol. 75, pp. 881-886.
Scott et al., "Searching for peptide ligands with an epitope library", *Science*, 1990, vol. 249, pp. 386-390.
Shimomura et al., "Identification of neuropeptide W as the endogenous ligand for orphan G-protein-coupled receptors GPR7 and GPR8", *J Biol Chem.*, 2002, vol. 277(39), pp. 35826-35832.
Tunaru et al., "PUMA-G and HM74 are receptors for nicotinic acid and mediate its anti-lipolytic effect", *Nat Med.*, 2003, vol. 9(3), pp. 352-355.
Wilson et al., "Orphan G-protein-coupled receptors: the next generation of drug targets?", *Br J Pharmacol.*, 1998, vol. 125, pp. 1387-1392.

(Continued)

*Primary Examiner* — Ruixiang Li

(57) ABSTRACT

Complexes of GPR81 receptor components and ligand components, such as L-lactate or GHB, may be used as an assay reagent for screening for modulators of GPR81 receptor activity.

5 Claims, 21 Drawing Sheets

OTHER PUBLICATIONS

Wong et al., "From the street to the brain: neurobiology of the recreational drug gamma-hydroxybutyric acid", *Trends Pharmacol Sci.*, 2004, vol. 25(1), pp. 29-34.

Zuckermann et al., "Discovery of nanomolar ligands for 7-transmembrane G-protein-coupled receptors from a diverse N-(substituted)glycine peptoid library", *J Med Chem.*, 1994, vol. 37, pp. 2678-2685.

Fang-Ming et al., "Molecular cloning, tissue distribution, and expression in engineered cells of human orphan receptor GPR81", *Chinese J Biotechnology*, 2006, vol. 22(3), pp. 408-412.

Ge et al., "Elucidation of signaling and functional activities of an orphan GPCR, GPR81", *J Lipid Res.*, 2008, vol. 49, pp. 797-803.

Figure 1

Human GPR81 coding region cDNA sequence (SEQ ID NO:31):

ATGTACAACGGGTCGTGCTGCCGCATCGAGGGGACACCATCTCCCAGGTGATGCCGCCGCTCATTGTGG
CCTTTGTGCTGGGCGCACTAGGCAATGGGGTCGCCCTGTGTGTTTCTGCTTCCACATGAAGACTTGGAAGCCC
AGCACTGTTTACCTTTTCAATTGGCCGTGCCGTGCTGATTCCTCCTATGATCTGCCTTTTCGACAGACTAT
TACCTCAGACGTAGACACTGGGCTTTTGGGGACATTCCCTGCCGAGTGGGCTCTTCACGTTGGCCATGAACA
GGGCCGGGAGCATCGTGTTCCTTACGGTGGCTGCGGACAGGTATTTCAAAGTGTTCACCCACCACGC
GGTGAACACTATCTCCACCGGGTGGCGCTGGCATCGTCTGCAAGAGACGGCCGTCTCCTGTGAGAGTCATCATGGAGTC
GCCAATGGCTGGCATGACATCATGTTCCAGGCGCAGCAGCTGGAGTTCTTTATGCCCCTCGGGATCATCCTTATTTTGCTCCTT
CAAGATTGTTGAGCCTCGAATTGTGTCATCACAAGTGCCCAGCGCTGGCATACCTTGTAGAGAAGGCGACCCGTT
CATCATGGTGGCCCCTCGAGTGCCTGCAGATCCCTCTGATTATTTCTTCAAGCCTGCACATAACCTCAGTCTCCTACGAAC
AGCATGCTGAAACCCAAGCAGGACAACCAGACACTCAAAAACACAAAGCCGAAGAGATGCCAATTCGAACCTCGG
CAGTCTGAAACCCAAGCAGGACAACCAGACACTCAAAAACACAAAGCCGAAGAGATGCCAATTCGAACCTCGG
TCGCAGGAGTTGCATCAGTGTGGCAAATAGTTCCAAAGCCAGTCTGATGGGCAATGGGATCCCCACATTGTT
GAGTGGCACTGA

Human GPR81 protein sequence (SEQ ID NO:32):

MYNGSCCRIEGDTISQVMPPLLIVAFVLGALGNGVALCGFCFHMKTWKPSTVYLFNLAVADFLLMICLPFRTDYY
LRRRHWAFGDIPCRVGLFTLAMNRAGSIVFLTVAADRYFKVVHPHHAVNTISTRVAAGIVCTLWALVILGTVY
LLENHLCVQETAVSCESFIMESANGWHDIMFQLEFFMPLGIILFCSFKIVWSLRRRQQLARQARMKKATRFIMV
VAIVFITCYLPSVSARLYFLWTVPSSACDPSVHGALHITLSFTYMNSMLDPLVYFSSPSFPKFYNKLKICSLKPKQ
PGHSKTQRPEEMPISNLGRRSCISVANSFQSQSDGQWDPHIVEWH

Figure 2

Rat GPR81L coding region cDNA sequence (SEQ ID NO:33):

ATGCTCTTCCTCTCTCCGAGTGCTATGGACAACGGGTCGTGTCTGTCTCATGGAGGGGAACCCATCACCCAGGT
AATGCCACCCTTTACTCATCCTGCTTCCTGCTTGGAGCCCTGGCCCTAGCCCTGTGTGTTTCTGCTT
TCACATGAAGACCTGGAAGTCGAGCACTATTTACCTTTCAACTTGGCTGTAGCCGATTTCTCCTCATGATCTG
CCTACCCCTTCCGACAGACTACTACCTCAGACGTAGGCATTGGATTTTGGGGGATATTCCCTGCCGCTGTCCT
CTTCATGCTGCCATGAATAGGGCCGGAAGCATTGTCTTCCTCACTGTGGTGGCCGTGCACAGGTATTTCAAAG
TGGTCCACCCCCACCATATGTGAACGCCATCTCCAATCGGACTGCAGCTGCCATCGTCTGTGTCCTCTGACTT
TGGTCATCTTGGGACTGTGTATCTTCTGATGGAGAGTCACCTGTGTGTGCGGGATGGTGTCATCTGTGAGA
GCTTCATCATGGAGTCAGCCAACGGGTGGCACGATATCATGTTCCAGCTGGAGTTCTCCTGCCCCTGACCATCA
TCTTGTTCTCCTTCAGATGTCATCATGGTGTTTGGAGCCTGGCTTCCGTTCATCACGTTCCTGCCCAGCGTGTTGGCGAGGCTC
AGGGCCACCGGTTCATCATGGTGCCCTCCAGTGCCTCCAGTGTGACCCTGCCCAGCTGTTACCTGCCCAGCGTGTTGGCGAGGCTC
TACTTCCTCTGGAGCGTGCCCTGTGACCCTCGTGACTCTGTGTACTTCTGTGACCCTCGTGACTCTGAGTCTC
ACCTACCTGAACAGCATGCTGGACCCTGAAACCCAGACGCTCGCAGGCAGGAGGTCGGAAGAGATGCCAATTT
CTCAAAATCTGTCGTAAGAGTTCCACCGATGTGGTAAATAGTTCCAGAGGCCGCTCTGACGCGGGCAGTGGGGTCTC
CAAGTGTGTTGA

Rat GPR81L protein sequence (SEQ ID NO:34):

MLFLSPSAMDNGSCCLIEGEPITQVMPPLLILAFLLGALGNGLALCGFCFHMKTWKSSTIYLFNLAVADFLMICLPL
RTDYYLRRRHWILGDIPCRLVLFMLAMNRAGSIVFLTVVADVRYFKVVHPHHMVNAISNRTAAAIVCVLWTLVILG
TVYLLMESHLCVRGMVSSCESFIMESANGWHDIMFQLEFFLPLTIILFCSFRVVWSLRQRQLTRQARMRRATRFIM
VVASVFITCYLPSVLARLYFLWTVPSSACDPSVHIALHVTLSLTYLNSMLDPLVYFSSPSFPKFYAKLKIRSLKPRRP
GRSQARRSEEMPISNLCRKSSTDVVNSSQRPSDGQWGLQVC

Figure 3

Rat GPR81S coding region cDNA sequence (SEQ ID NO:37):

ATGGACAACGGGTCGTGCTGTCTGATCGAGGGGGAACCCATCACCCAGTAATGCCACCTTTACTCATCCTGGC
CTTCCTGCTGGAGCCCTGGGCAACGGCCTAGCCCTGTGGTTTCTGCTTCACATGAAGACCTGAAGTCGAG
CACTATTTACCTTTCAACTTGGCTGTAGCCGATTTCTCCTCATGATCTGCCTACCCCTTCGGACAGACTACTAC
CTCAGACGTAGGCATTGGATTTTGGGGGATATTCCCTGCCGGTGGTGGCCGTGACAGTATTCAAAGTGGTCCACCCCACCATATGGTGAA
GGAAGCATTGTCTTCCTCACTGTGGTGGCCGTGACAGTATTCAAAGTGGTCCACCCCACCATATGGTGAA
CGCCATCTCCAATCGGACTGCCAGCTGCCATCGTGTGTCCTCTGACTTTGGTCATCTTGGGACTGTGTATCT
TCTGATGGAGAGTCACCTGTGTGCGGGGGATGGTCTTCCTGGAGTTCTTCCTGCCCCTGACCATCATCTGTGAGACGATATCATGTTCCAGTGGTCTTCCTGGAGTTCTTCCTGCCCCTGACCATCATCTGTTCTGCTCCTTCAGAGTTGT
GTGGAGCCTGAGACAGAGGCAACAGCTCCCAGGCGTGTTGGCGAGCTCTACTTCCTCTGACGGTGCCCTCC
AGTGCCTGTGACCCCTCTGTCCACATAGCTCTGTCCACATAGCTCTCCATGTCACCCTGAGTCCATGTCTGAACAGCATGCTGGAC
CCTCTGTGTACTACTCTCGAAGCCCCGTTCCGCAGGACGCTCGCAGGACGCTCGCAGGACGCTCGACGAGGGCCGTCTGACGAGGGCCGTCTGACGAGGGCCGTCGACGCGGAAACCC
AGACGCCCAGGACGCTCGCAGGACGCTCGACGAGGGCCGTCTGACGAGGGCCAGTGGGGTCTCCAAGTGTGTTGA
CGATGTGGTAAATAGTTCCCAGAGGCCGTCTGACGAGGGCCAGTGGGGTCTCCAAGTGTGTTGA

Rat GPR81S protein sequence (SEQ ID NO:38):

MDNGSCCLIEGEPITQVMPPLLILAFLLGALGNGLALCGFCFHMKTWKSSTIYLFNLAVADFLLMICLPLRTDYYLR
RRHWILGDIPCRLVLFMLAMNRAGSIVFLTVVAVDRYFKVVHPHHMVNAISNRTAAAIVCVLWTLVILGTVYLLM
ESHLCVRGMVSSCESFIMESANGWHDIMFQLEFFLPLTIILFCSFRVVWSLRQRQQLTRQARMRRATRFIMVVASVFI
TCYLPSVLARLYFLWTVPSSACDPSVHIALHVTLSLTYLNSMLDPLVYFSSPSFPKFYAKLKIRSLKPRRPGRSQAR
RSEEMPISNLCRKSSTDVVNSSQRPSDGQWGLQVC

Figure 4

Mouse GPR81L coding region cDNA sequence (SEQ ID NO:35):

ATGCCAGTCCTCTCTCCAACTGCTATGGACAACGGGTCGTGTCTCATCGAGGGGAGCCCATCTCCAAGTGATG
CCTCCTCTACTCATCCTCGTGTTCGTGCTTGGCGCCTTGGGCGCCAACGGCATAGCCCTGTGCGGCTTCTGCTTTCACATGA
AGACCTGGAAGTCAAGCACTATTACCTTTCAACTTTCTCCTCATGATCTGCTTACCCCTCG
GACAGACTACTACCTCAGAGACGAGCAGACACTGGATTTTTGGAGATATGCGTGCGCCTGTCTCTTCAAGTCTGGCCAT
GAATAGGGCCGGGAGCATTGTCTTCCTCACTGTCGTGGCTGTGATAGGTATTTCAAAGTGGTCCACCCACCATAT
GGTGAATGCCATCTCCAACGGACTGCCGCCCACTGTCGTCGTGCAGGGACACTGTCGTCCTGTGAGAGCTTCATCATGGAGTCAGCCAACG
TCTTCTGATGGAGAGTCACGATGTCATGTTCCAGTGTCGAGTTCTTCCTGACAATCATCTTGTTCTCGGTCAACGTTGTTG
GAGCCTGAGACGAGGAGCAGCAGTCTGAGAGCTCGGCTAGGCTGTGGCTGTGGCTACCGTTCATCATGTGGTGGCT
TCTGTGTTCATCACGTGTTACCTGCCCAGCGGTGCGGGCTAGCCTCCTCTGGACGGTGCCCACTAGTGCCTGT
GACCCCTCTGTCCACACAGCCTGCGCTCCCAAGTCCAGTCCAGTTCTGAGCTTCACCTGACGTATGCTGGATCCCCTTGTATAT
TACTTCTCAAGCCCTCGCTCCCCCAAATTCTACCAAGTCACAATCTGCGGCAGCCCAAACGCCCAGGACG
CACGAAGACGCGGAGGTCAGAAGAGAAGATGCCAATTTCGAACCTCTGCAGTAAGAGCTCCATGATGGGGCAAATCGTT
CCCAGAGGCCATCTGACGGGCAGTGGGATCTCCAAGTGTGTTGA

Mouse GPR81L protein sequence (SEQ ID NO:36):

MPVLSPTAMDNGSCCLIEGEPISQVMPPLLILVFVLGALGNGIALCGFCFHMKTWKSSTIYLFNLAVADFLLMICLPL
RTDYYLRRRHWIFGDIACRLVLFKLAMNRAGSIVFLTVVAVDRYFKVVHPHHMVNAISNRTAAATACVLWTLVIL
GTVYLLMESHLCVQGTLSSCESFIMESANGWHDVMFQLEFFLPLTIILFCSVNVVWSLRRRQQLTRQARMRRATRFI
MVVASVFITCYLPSVLARLYFLWTVPTSACDPSVHTALHVTLSFTYLNSMLDPLVYFSSPSLPKFYTKLTICSLKPK
RPGRTKTRRSEEMPISNLCSKSSIDGANRSQRPSDGQWDLQVC

Figure 5

Mouse GPR81S coding region cDNA sequence (SEQ ID NO:39):

ATGGACAACGGGTCGTGTCTGTCTTGAGGGGAGCCCATCTCCAAGTGATGCCTCCTCTACTCATCCTGTCTTC
GTGCTTGGGCGCCTGGGCCCTGTGCGCTTGCGGCTTCACATGAAGACCTGCACATGAAGACCTTCACAGCACTATT
TACCTTTCAACTTGGCTGTGGCCGATTTTCTCCTCATGATCTGTCTTACCCCTTCGGACAGACTACTCAGACGCA
GACACTGATTTTTGGAGATATCGCCCTGTGCCTGTCCTCTTCAAGCTGGCCATGAATAGGGCGGAGCATTGTCT
TCCTCACTGTGGTGGCCGTGTGTGGATAGGTATTCAAAAGTGGTCACCCACCATATGTGTGAATGCCATCCAACGGA
CTGCCGCCGCCACGCCTGTCCTCTGGACTTTGGTCATCTTGGGACTGTGTATCTTCTGATGGAGAGTCACCTGT
GTGTGCAGGGGACACTGTCGTCCTGACAATCATCTTGTTCTGCTCGGTCAACGTTGTTGGAGCCTGAGACGGAGGCAGCAG
CTGACCAGACAGGCTGGCTAGCTCTACTTCCTGGATGAGAGGCCACCCGGTTCATCATGTGGTGGCTTCGTTGTTCATCACGTGTTACCTG
CCCAGCGTGCTGAGCTTCACCTACCTGGAACAGTATGCTGGATCCCCTGTATATTACTTCTCAAGCCCCTCGCTCCCC
CACGTCACCCTGGTGAGCTTCACCTACCTGGAACAGTATGCTGGATCCCCTGTATATTACTTCTCAAGCCCCTCGCTCCCC
AATTCTACACCAAGTCACAATTCGAACCTCTGCAGTAAGAGCTCCATGATGGGCAATCGTTCCCAGAGGCCATCTGACGGGCAG
AGATGCCAATTCGAACCTCTGCAGTAAGAGCTCCATGATGGGCAATCGTTCCCAGAGGCCATCTGACGGGCAG
TGGGATCTCCAAGTGTGTGTTGA

Mouse GPR81S protein sequence (SEQ ID NO:40):

MDNGSCCLIEGEPISQVMPPLLILVFVLGALGNGIALCGFCFHMKTWKSSTIYLFNLAVADFLLMICLPLRTDYYLRR
RHWIFGDIACRLVLFKLAMNRAGSIVFLTVVAVDRYFKVVHPHHMVNAISNRTAAATACVLWTLVILGTVYLLME
SHLCVQGTLSSCESFIMESANGWHDVMFQLEFFLPLTIILFCSVNVVWSLRRQQLTRQARMRRATRFIMVASVFI
TCYLPSVLARLYFLWTVPTSACDPSVHTALHVTLSFTYLNSMLDPLVYFSSPSLPKFYTKLTICSLKPKRPGRTKTR
RSEEMPISNLCSKSSIDGANRSQRPSDGQWDLQVC

Figure 6

Bovine GPR81 coding region cDNA sequence (SEQ ID NO:41):

ATGGCCAACAGGTCGTGTCTGTCTCATCCAGGGGTACCACATGCCGAGGTGATGCCGTCGCTGCTAATCCTCGCCTTTG
TGCTCGGCATCCTGGGCAACGGCGTCGCCCTCTGTGGTTTCTGCTTTCACATGAAGACCTGGAAGCCGAGCACTATTTA
CCTGTTCAACTTGGCCGTGGCCGACTTCCTTCTGATGATCTGCCTGCCTTTCCGGACACGACTACTCAGACAGAGG
CAATGGGCGTTTGAGGATATCCTTGCGGTGGTGCTCTTCATGCTGGCCATGAACAGGGCGGGAGCATTGTCTTCC
TCACAGTGGTGCTGTGACCGGTATTTAAAGTGGTCCACCCCACCACATGTGAACACCATCTCAACTGGACTG
CGGTTGGCATTGTCTGTCGTCCTTTGGGACTCTGTCATCTTGGGGACTCTGTATCTTCTGTTGGAGAACCATCTGTGTG
CAAGAGAAGATCATAGCTGTGAGAGCTTCATCATGGCTGCCCTCAAGATCATTGGAGCCTCAAGAGGCAGCGTCTGGCCA
TTCTTTCTGCCCCTTGGCATCATCTGTTCTGCTTCGTTCATCATGAGCCTGCTGCGGTGTGTTTATTGCCTGCTCAACTGCAC
GGCAGAGCCGATGAAGAAGCCTCTCTGGACGGTGCCCTGCAATCATCGTCCATGTGGCCCTCCACGTCAC
CGTTGGCCAGAGTGTATTCCTCGGACGGTGCCCTCCAAGCGCCAATCATCGTCCATGTGGCCCTCCACGTCAC
CCTCAGTCTTCACCTACATAAACAGCATGCTGGACCTAGGGTGTGAGAACCTAGGGTGTCCGGGATGCTTCAAGAGGCCAGAGGGACAGAGGGGATGCCCACTCCAA
ACCAAGCTCAAAATCTGCAGTGTGAGACCTAGGGTGTCCGGGATGCTTCAAGAGGCCAGAGGGACAGAGGGGATGCCCACTCCAA
CCTTTGTTGCAAGAGT TGCATCAGTGTTGCAAATAGCTTCCAAAGCCAGTCTGAGGGGCAGTGA

Bovine GPR81 protein sequence (SEQ ID NO:42):

MANRSCCLIQGYHMPEVMPSLLILAFVLGILGNGVALCGFCFHMKTWKPSTIYLFNLAVADFLLMICLPFRTDYLRQRQW
AFEDIPCRVVLFMLAMNRAGSIVFLTVVAVDRYFKVVHPHHMVNTISNWTAVGIVCVLWTLVILGTLYLLLENHLCVQEKI
IACESFIMVSANGWHDVMFQLEFFLPLGIILFCSFKIIWSLKQRQRLARQSRMKKPVRFIMMVAVVFIACYLPSALARLYFLW
TVPSSACNPSVHVALHVTLSFTYINSMLDPLVYFSSPSFPKFYTKLKICSVRPRCPGCFKRPEGMPTSNLCCKSCISVANSFQ
SQSEGQ

Figure 7

Dog GPR81 coding region cDNA sequence (SEQ ID NO:43):

ATGGACAACGGGTCGTGCTGCCTCATCGAGGGGGACCCCATCTCTCAGGTGATGCCACCGCTGATCCTGGCC
TTCGTGCTGGGCGCACTGGGCAATGGCATGGCCCTCTGTGTTCTGTTTCTGTTTTACATGAAGACCTGGAAGCCGAGC
ACTATTTACCTTTTTAACCTGGCCGTGCCGACTTCCTCTCATGATCTGCCTCTGCCTTCCGACAGACTACTACT
GGAGACACAGGCAATGGGCCTTTGAGGACATTCCGTGTCGGGTGGCCTCTTCATGTCGGCCATGAACAGGCTG
GGAGCATCATCTTCCTACTGTGGTTGCGGTGGACAGGTACTTCAAAGTGGTCCACCCACCACGTGCTGAACA
CCATTTCCAACCGGACTGCAGCTGGCATCGTCTGTGCCCTTTGGATCATGTCATGGAGAGCTTCATGATGTTT
GATGGAGAACCATCTGTGCGTGCAGCTGGAATTCTTCCTCCTGCCATCATCTGTGCTCCTTCAGGATTATTGG
GCACGACATCATGTTCCAGTGGCAGCGGGCAGCTGCCAGGCAGCTGATGAAGAAGGCTACCCGGTTCATCATGGTTGTGGC
AGTCTGAAGCAGAGGCGCAGAGCTCATCAGGTGTCATGGCCGATGAAGCTCTATTCCCTCTGGACGGTGCCCTCGAGTGCC
GGTTGTGTCATCAGCGTTGCTCCACGTAGCCCTCCACATCACCCTCAGCTTCACCTACAGATCGCGGTTTGCGACCAAAGAGTCC
TGCGACCCCTCTGTCCACGTAGCCCTCCACATCACCCTCAGCTTCACCTACAGATCGCGGTTTGCGACCAAAGAGTCC
TGTATTATTTTCGAGTCCTGTATTCCCAAATTCTACCAAGCTCAACAAGCTCTGTGCAAGAGTTGTGTCCGTGTGG
AGGGCACTCCAGAACCCAAGAGGCCGAAGAGATGCCAATCCAAAGCTCCAAAGCTCTTCAAATGTGTGGAATGCACTGAAACAGGCAGAC
CAAGCAGCTTCCAGAGCCAATCCAACGAGCAGGATCTTCAAATGTGTGGAATGCACTGAAACAGGCAGAC
AGGCAAAACCCAAGGAGGAGGACAGACAAACAGACTTAG

Dog GPR81 protein sequence (SEQ ID NO:44):

MDNGSCCLIEGDPISQVMPPLLILAFVLGALGNGMALCGFCFYMKTWKPSTIYLFNLAVADFLLMICLPFRTDYYW
RHRQWAFEDIPCRVALFMLAMNRAGSIIFLTVAVDRYFKVVHPHHVLNTISNRTAAGIVCALWIMVILGTLYLLM
ENHLCVHEKTISCESFIMESANGWHDIMFQLEFFLPLGIILFCSFRIIWSLKQRRQLARQTRMKKATRFIMVAVVFIT
CYLPSVSARLYFLWTVPSSACDPSVHVALHITLSFTYMNSMLDPLVYFSSPVFPKFYTKLKIRGLRPKSPGHSKTQR
PEEMPIPKLCRKSCVRVASSFQSQSNEQQDLQMCGMALKQADRQNPRRTDKQT

Figure 8

Monkey GPR81 coding region cDNA sequence (SEQ ID NO:45):

ATGTACAACGGGTCGTGCTGCCGCATCGAGGGGGACACCATCTCCCAGGTGATGCCGCCGCTCATTGTG
GCCTTTGTGGGCGCACTAGGCAATGGGGTCGCCCTGTGTGGTTTCTGCTTCCACATGAAGACCTGGAAGC
CAAGCACTGTTACCTTTCAACTGGCCGTGCTGGCTTTGGGGACATTCCCTGCCGGGTGGGGCTCTTCACCTTGGCCATGA
TATTACCTCAGAGACGTAGACACTGTGTTCCTTACGGTGGTGGCTGTGACAGGTATTTCAAAGTGGTCCACCCCACC
ACGGGCCGGGAGCATCGTGTTCCTTACGGTGGTGGCTGTGACAGGTATTTCAAAGTGGTCCACCCCACC
ACGCGGTGAACACCATCTCCAACCGGACGGCAGCTGGCATCGTCTGCACCCTGTGACCCTGGTCATCCTGG
GAACACTGTATCTTTTGCTGAGAACCATCTCTGTGTGCAAGACGCGTCTTCTGCCCCTCGGCATCATCTTATTT
GGAGTCGGCCAATGCTGGCATGACATGTTCCAGCTGGAGCAGCAGCCAGACAGGCTCGGATGAAGAAGGCGA
GCTCCTTCAAGATTGTTGGAGCCGGCAGTGTTCATCACGTGCTACCTGCCCAGCTGTCCCCAGACTCTATTC
CCCGGTTCATCATGGTGGCAGTTGTTCATCACGTGCTACCTGCCCAGCTGTCCCCAGACTCTATTC
CTCTGGACGGTGCCCTGAGTCGCCTGCGATCCCCTGGTCGATTTTTTCAAGCCCCTGGTTCCCAAATTCTACAACAAGCT
ACATGAACAGACATGCTGATCCCCTGGTATTATTTTCAAGCCCCTGGTTCCCAAATTCTACAACAAGCT
CAAAATCTGCAGTCTGAAACCTCAAACACACTCAAAACACAAGGCCGCAAGAGATGCCAATTT
CGAACCTCAGTCGCAAGAGTTGCCCTCAGTGTGACAACTAGTTCCCAAGCCAGTCTGATGGGCAGTAG

Monkey GPR81 protein sequence (SEQ ID NO:46):

MYNGSCCRIEGDTISQVMPPLLIVAFVLGALGNGVALCGFCFHMKTWKPSTVYLFNLAVADFLLMICLPFRTDYY
LRRRHWAFGDIPCRVGLFTLAMNRAGSIVFLTVAVDRYFKVVHPHHAVNTISNRTAAGIVCTLWTLVILGTLYL
LLENHLCVQETAVSCESFIMESANGWHDIMFQLEFFLPLGIILFCSFKIVWSLRRQQLARQARMKKATRFMVVA
VVFFITCYLPSVSARLYFLWTVPSSACDPSVHVALHITLSFTYMNSMLDPLVYFSSPSFPKFYNKLKICSLKPKQPG
HSKTQRPQEMPISNLSRKSCLSVTTSSQSQSDGQ

Figure 9

Porcine GPR81 coding region cDNA sequence (SEQ ID NO:47):

ATGGACAACGGGTCATGCTGCCTCATCCAGGGGGACCCTATCTCCCAGGCGATGCCGCCGCTGCTGATCCTGGCCTT
CGTGCTCGGTGCCCTGGGCAACGGTATCGCCCTGTGTGGATTTGCTTTCACATGAAGACCTGGAAGCCCAGCACTA
TTAACCTTTTCAACTTGGCTGTGGCTGACTTTCTTCTCATGATCTGCCTTCGACGGACTATTACCGCAGAC
ACAGGCAATGGGCCTTTGGGATATTCCCGTGACAGTATTTAAAGTGTCCACCCCACCATATGTGAATGCCATCTCCA
ACCGGACCGCAATTGGCATCGTCGCCCTTTGGACACTGTCATCGAGGGACTCTGTATCTTTTGATGGAGAAC
CATCTGTGTGCAAGAAGAAGACCATAGCTGTGAGAGCTTCATCATGAGTCAGCAGTCTGGCATGAGCTCA
TGTTCCAGCTGTTCCTGCCCCTGGCATCATCTTGTCTGCTCAAGGTCATTTGGAGCCTGGAGCAGA
GGCAGCACCTGGCCAGGCAGGTCGATGAAGAGGGCTACACGGTCATCGTGGTGCAGTTGTTCATCAC
GGGCTACCTGCCTAGCGGTGTCAGCAGACCCTCAGCTTCACCCTCAGTCAACAGCATGCTTGGACCCCTCTGTGC
ATGTAGCCCTCCATGTCAACCCTCAGTTCAACCTCCACTCACATGAACAGCATCTGAGACCTAAGCTCAAGTC
CCTGGTCCCCAAATTCTACTCCAAGCTCAAGATCTGCACAAGAGTTGCATTAGTGTGGCAAATGTTCCAAGTCAATCAGATG
GAAGAGATGCCAATTCAATTCAACCTTTGTCACAGAGTTGCATTAGTGTGGCAAATGTTCCAAGTCAATCAGATG
TGCAGTGGGATCCCCAGATGTGA

Porcine GPR81 protein sequence (SEQ ID NO:48):

MDNGSCCLIQGDPISQAMPPLLILAFVLGALGNGIALCGFCFHMKTWKPSTIYLFNLAVADFLLMICLPFRTDYYRRHR
QWAFGDIPCRAVLFMLAMNRAGSIVFLTVAVDRYFKVVHPHHMVNAISNRTAIGIVCALWTMVIVGTLYLLMENHL
CVQEKTIACESFIMESANGWHDVMFQLEFFLPLGIILFCSFKVIWSLEQRQHLARQARMKRATRFIVVAVVFITGYLPS
VSARLYFLWTVPSSVCDPSVHVALHVTLSFTYMNSMLDPLVYFSSPSFPKFYSKLKICSLRPKHPGRSKRPEEMPISNL
CHKSCISVANSFQSQSDVQWDPQM

Figure 10

```
Human GPR81                                                              MLFLSPSA    8
  Rat GPR81L                                                              MPVLSPTA    8
Mouse GPR81L
    Consensus    M NGSCC  IEG+   ISQVMPPLLI ++F +LGALGNG+   ALCGFCFHMKTWK  ST+YLFNLAVA
                                                                              TM2

Human GPR81  MYNGSCCRIEGDTISQVMPPLLIVAFVLGALGNGVALCGFCFHMKPSTVLFNLAVA   60
  Rat GPR81L MDNGSCCLIEGEPITQVMPPLLILAFLLGALGNGLALCGFCFHMKTWKSSTIYLFNLAVA 68
Mouse GPR81L MDNGSCCLIEGEPISQVMPPLLILVFVLGALGNGIALCGFCFHMKTWKSSTIYLFNLAVA 68
    Consensus                                                                 TM1

Human GPR81  DFLLMICLPFRTDYYLRRRHWAFGDIPCRVGLFTLAMNRAGSIVFLTVVAADRYFKVVHP 120
  Rat GPR81L DFLLMICLPLRTDYYLRRRHWILGDIPCRLVLFMLAMNRAGSIVFLTVVAVDRYFKVVHP 128
Mouse GPR81L DFLLMICLPLRTDYYLRRRHMIFGDIACRLVLFKLAMNRAGSIVFLTVVAVDRYFKVVHP 128
    Consensus DFLLMICLP+RTDYLRRRHW++GDI CR+ LF LAMNRAGSIVFLTVVA+DRYFKVVHP
                                                TM3

Human GPR81  HHAVNTISTRVAAGIVCTLWALVILGTVYLLLENHLCVQETAVSCESFIMESANGWHDIM 180
  Rat GPR81L HHMVNAISNRTAAAIVCVLWTLVILGTVYLLVYLLMESHLCVRGMVSSCESFIMESANGWHDIM
Mouse GPR81L HHMVNAISNRTAAATACVLWTLVILGTVYLLVYLLMESHLCVQGTLSSCESFIMESANGWHDVM 188
    Consensus HH+VN IS R AA +C LW LVILGTVYLL+E+HLCV  ++ SCESFIMESANGWHD+M
                                    TM4

Human GPR81  FQLEFFMPLGIILFCSFKIVWSLRRRQQLARQARMKKATRFIMVAIVFITCYLPSVSAR   240
  Rat GPR81L FQLEFFLPLTIILFCSFRVVWSLRQRQQLTRQARMRRATRFIMVUASVFITCYLPSVLAR
Mouse GPR81L FQLEFFLPLTIILFCSVNVVWSLRRRQQLTRQARMRRATRFIMVUASVFITCYLPSVLAR 248
    Consensus FQLEFF+PL  IILFCS+    +VWSLRRRQQL RQARM++ATRF IMVVA  VFITCYLPSV AR
                 TM5

Human GPR81  LYFLWTVPSSACDPSVHGALHITLSFTYMNSMLDPLVYFSSPSFPKFYNKLKICSLKPK  300
  Rat GPR81L LYFLWTVPSSACDPSVHIALHVTLSLTYLNSMLDPLVYFSSPSFPKFYAKLKIRSLKPR
Mouse GPR81L LYFLWTVPTSACDPSVHTALHVTLSFTYLNSMLDPLVYFSSPSLPKFYTKLTICSLKPK 308
    Consensus LYFLWTVP+SACDPSVH ALH+TLS+TY+NSMLDPLVYFSSPS+PKFY KL I SLKPK
                                           TM7

Human GPR81  QPGHSKTQRPEEMPISNLGRRSCISVANSFQSQSDGQWDPHIVEWH                346
  Rat GPR81L RPGRSQARRSEEMPISNLCRKSSTDVVNSSQRPSDGQWGLQVC                  351
Mouse GPR81L RPGRTKTRRSEEMPISNLCSKSSIDGANRSQRPSDGQWDLQVC                  351
    Consensus +PG ++ +R EEMPISNL  +S+ +R    P SDGQW
```

METHODS OF IDENTIFYING MODULATORS OF GPR81 RECEPTORS

CROSS-REFERENCE TO RELATED APPLICATIONS

This is a continuation-in-part of prior International Application No. PCT/US2007/021924, filed Oct. 11, 2007, which claims priority to U.S. Provisional Application No. 60/851,681, filed Oct. 13, 2006.

FIELD OF THE INVENTION

The present invention relates to complexes of GPR81 as the receptor material and L-lactate or a mimetic thereof, such as GHB, as the ligand material, and the preparation and use of such receptor-ligand complexes. Also described are various GPR81 polypeptides, such as rat-L, mouse-L, pig, and monkey proteins, which may be used as the receptor component of such a complex.

BACKGROUND OF THE INVENTION

To facilitate an appreciation of the invention, this section may discuss the historical and technical background leading to the development of the invention, including observations, conclusions, and viewpoints that may be unique to an inventor. Accordingly, the background statements herein should not be construed as an admission regarding the content of the prior art.

Gamma-hydroxybutyric acid (GHB) is a putative neuromodulator that has profound physiological, pharmacological and biochemical effects in the brain and the peripheral system (Maitre, *Prog. Neurobiol.*, Vol. 51, pp. 337-361 (1997)). The functions of γ-hydroxybutyric acid in the brain include anxiolytic effect, sleep modulation, anesthesia, and absence seizures. In addition, GHB regulates the neurotransmitter release of dopamine, opioids, glutamates and acetylcholine.

GHB has been used as an anesthetic agent for treating sleep disorder and alcohol dependence (see, e.g., Gonzalez, *Psychopharmacology*, Vol. 19, pp. 195-204 (2005), and Wong et al., *Trends Pharmacol. Sci.*, Vol. 25, pp. 29-34 (2004)). GHB has been marketed as a bodybuilding and fat burning compound. Due to its euphoric effects, GHB has the potential for abuse (Bernasconi et al., *TiPS*, Vo. 20, pp. 135-141 (1999)). In 1990 GHB was banned for non-prescription sale, and in 2000 GHB was classified as a schedule I drug by the U.S. Food and Drug Administration.

GHB's mechanism of action remains to be established. Bernasconi et al. (1999) have suggested that the receptor for GHB is a $GABA_B$ receptor (Bernasconi et al., 1999). Others have merely postulated that GHB's receptor is a GPCR (Andriamampandry et al., *The FASEB Journal*, Vol. 17, pp. 1691-1693 (2003).

G-protein coupled receptors (GPCRs) are transmembrane receptor proteins that are responsible for the transduction of a diverse array of extracellular signals, including hormones, neurotransmitters, peptides, lipids, ions, light, odorants, nucleotides, fatty acid derivatives, and other chemical mediators (see, e.g., International Publication No. WO 02/00719). GPCRs are of particular importance to drug discovery because they have been established as excellent drug targets: they are the targets of 50% of marketed drugs. An increasing number of diseases have been found to be associated with GPCRs. Drugs targeting GPCRs have been used to treat a wide range of disorders from cardiovascular to gastro-intestinal to central nervous system (CNS) and others (Wilson et al., 1998, *British J. of Pharmacology* 125:1387-1392).

The GPCR-mediated signal transduction event is often initiated upon binding of a specific ligand to the GPCR. Each GPCR is composed of an extracellular N-terminal domain, seven distinct transmembrane segments, and an intracellular C-terminal domain. Binding of the ligand to the extracellular N-terminal domain of GPCR results in a conformational change that leads to activation of intracellular heterotrimeric GTP-binding proteins (G proteins) associated with the GPCR. These activated G proteins in turn mediate a variety of intracellular responses that regulate the cell physiology. Therefore, the ligand provides means of elucidating the physiological function of the GPCR as well as methods of screening for compounds that regulate the signal transduction activity of the GPCR.

Through sequence analyses, it was discovered that GPCRs belong to one of the largest superfamilies of the human genome: evaluated at over 1000 genes encoding GPCRs (see Civelli et al., 2001, *Trends in Neurosciences* 24:230-237; United States Patent Application Publication No. US 2003/0171541). A large number of putative GPCRs are described as orphan receptors because their natural ligands are unknown. Some of these uncharacterized orphan GPCRs may be useful as therapeutic targets. The identification of the specific ligand for a GPCR is the key to harnessing the potential benefits of these orphan GPCRs as potential therapeutics (Howard et al., 2001, *Trends in Pharmacological Sciences* 22:132-140) or drug discovery tools.

GPR81, also known as GPCR104, is an orphan G-protein coupled receptor (GPCR) (Lee et al., *Gene*, Vol. 275, pp. 83-91 (2001); see also US Patent Application Publication No. 2003/0171541). The receptor is up-regulated during T-cell activation (Mao et al., *Genomics*, Vol. 83(6), pp. 989-999 (2004)). GPR81 shares about 70% homology to nicotinic acid receptor HM74A and HM74; however, nicotinic acid does not activate GPR81 (Tunaru et al., *Nat. Med.*, Vol. 9(3), pp. 352-355 (2003)). GPR81 is expressed in many tissues and highly expressed in fat and lymph nodes, and therefore this receptor is expected to play an important role in metabolism and immune functions. There is a desire to identify the endogenous ligand for GPR81, as this would facilitate the targeted development of pharmaceutical treatments for diseases and disorders mediated through modulation of this receptor's activity.

SUMMARY OF THE INVENTION

The results of experiments described below reflect that L-lactate is the endogenous ligand for GPR81. Moreover, experimental results described below reflect that GHB also activates GPR81. Consequently, ligand complexes with GPR81 may be used in drug screening assays to identify compounds for treating diseases, disorders, and medical conditions mediated by GPR81 modulation, such as sleep disorders, alcohol dependence, diabetes, obesity, lactate acidosis, high blood levels of cholesterol or hyperlipidemia, congestive heart failure, Huntington's disease, metabolic disorders, cancers, central nervous system associated diseases, diseases mediated by one or more growth hormone deficiencies, drug abuse, lactate induced panic attacks, immune disease, and diseases moderated by collagen degradation, such as skin wrinkling and aging.

Accordingly, the invention is directed to the general and preferred embodiments defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

BRIEF DESCRIPTION OF THE DRAWINGS

FIG. 1 illustrates human GPR81 receptor coding region cDNA (SEQ ID NO:31) and the encoded human GPR81 receptor amino acid sequence (SEQ ID NO:32).

FIG. 2 shows rat GPR81L receptor coding region cDNA (SEQ ID NO:33) and the encoded rat GPR81L receptor amino acid sequence (SEQ ID NO:34).

FIG. 3 illustrates rat GPR81S receptor coding region cDNA (SEQ ID NO:37) and the encoded rat GPR81S receptor amino acid sequence (SEQ ID NO:38).

FIG. 4 illustrates mouse GPR81L receptor coding region cDNA (SEQ ID NO:35) and the encoded mouse GPR81L receptor amino acid sequence (SEQ ID NO:36).

FIG. 5 shows mouse GPR81S receptor coding region cDNA (SEQ ID NO:39) and the encoded mouse GPR81S receptor amino acid sequence (SEQ ID NO:40).

FIG. 6 illustrates bovine GPR81 receptor coding region cDNA (SEQ ID NO:41) and the encoded bovine GPR81 receptor amino acid sequence (SEQ ID NO:42).

FIG. 7 illustrates dog GPR81 receptor coding region cDNA (SEQ ID NO:43) and the encoded dog GPR81 receptor amino acid sequence (SEQ ID NO:44).

FIG. 8 shows monkey GPR81 receptor coding region cDNA (SEQ ID NO:45) and the encoded monkey GPR81 receptor amino acid sequence (SEQ ID NO:46).

FIG. 9 illustrates porcine GPR81 receptor coding region cDNA (SEQ ID NO:47) and the encoded porcine GPR81 receptor amino acid sequence (SEQ ID NO:48).

FIG. 10 provides a sequence alignment comparing the amino acid sequences for human GPR81, rat GPR81L, and mouse GPR81L.

FIG. 15A: results of preparative HPLC of crude porcine brain extract. FIG. 15B: results of $^{35}$S-GTPγS binding assays employing GPR81-expressing membranes and the indicated HPLC fractions. FIG. 15C: results of $^{35}$S-GTPγS binding assays employing membranes not expressing a GPCR and the indicated HPLC fractions.

DETAILED DESCRIPTION OF INVENTION AND ITS PREFERRED EMBODIMENTS

Figure 11:
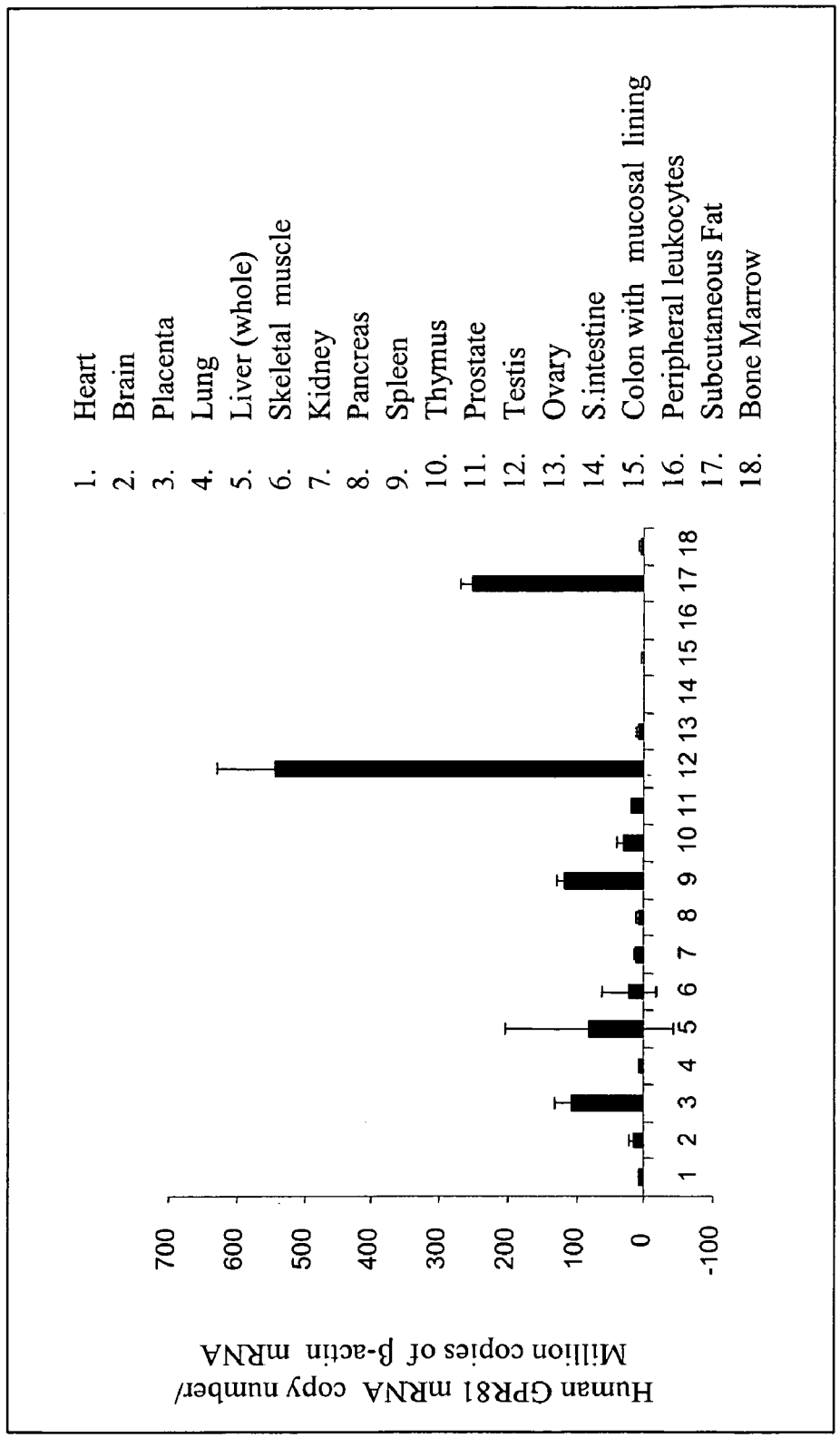
FIG. 11 depicts the expression levels of human GPR81 mRNA in the indicated tissues, as determined by quantitative PCR.

To illustrate various aspects and advantages of the invention, exemplary and preferred embodiments are described below. For the sake of brevity, the disclosures of all patents and other publications cited in this specification are incorporated by reference herein. Unless defined otherwise herein or apparent from the context, all technical and scientific terms used herein have the same meaning as used in the art.

The terms "including", "comprising", and "containing" are used herein in their open, non-limiting sense.

The following are abbreviations that may be at times used in this specification: bp=base pair; $Ca^{2+}$=calcium ion; cAMP=cyclic adenosine monophosphate; cDNA=complementary DNA; GTP=guanosine 5'-triphosphate; PCR=polymerase chain reaction; SDS=sodium dodecyl sulfate.

In one general aspect, the invention is directed to a receptor-ligand complex comprising a receptor component in substantially isolated or in a substantially pure form complexed with a ligand component.

A "receptor component" as used herein means a protein or polypeptide that is a GPR81 from an animal species having at least 60% homology to human GPR81. Preferably, the receptor component comprises a GPR81 protein that is originated from an animal, more preferably one having at least 80% homology or sequence identity to human GPR81. A polypeptide can exist as a full-length nascent or unprocessed polypeptide, or as partially processed polypeptides or combinations of processed polypeptides. The full-length nascent polypeptide may be post-translationally modified by specific proteolytic cleavage events that result in the formation of biologically active fragments of the full-length nascent polypeptide.

Preferably, the receptor component is selected from human, monkey, dog, cow, pig, mouse, rat, and fugu fish GPR81. More preferably the receptor component is from a mammalian species, even more preferably human. Preferred receptor components are human, monkey, canine, bovine, porcine, canine, murine, and rat GPR81 polypeptides. In particularly preferred embodiments the polypeptide of the receptor component has an amino acid sequence as set forth in SEQ ID NO:32, SEQ ID NO:34, SEQ ID NO:36, SEQ ID NO:38, SEQ ID NO:40, SEQ ID NO:42, SEQ ID NO:44, SEQ ID NO:46, or SEQ ID NO:48.

The "ligand component" is L-lactate or a mimetic thereof, i.e., a chemically similar compound that has significant agonist activity against GPR81. Preferably, the ligand component is a compound selected from L-lactate, D-lactate, α-hydroxybutyrate, GHB, hydroxyisobutyrate, glycolic acid, dichloroacetate (DCA), trifluoroacetate (TFA), chlorodifluoroacetate (CDFA), 2-chloropropinoic acid (CPA), or 2-chloropropionic acid, or a salt of any of the aforementioned acids.

In preferred embodiments, the receptor and ligand components are each in substantially pure form. The term "substantially pure form" as used herein in reference to a complex or a component thereof means that it is essentially free of contaminating matter (e.g., cellular matter, contaminating proteins, chemical precursors) that would interfere with ligand-receptor binding. For example, a receptor polypeptide prepared recombinantly in substantially pure form contains less than about 20%, or preferably 10%, 5%, or 1%, by dry weight of cellular matter, other proteins, chemical precursors, or other contaminants. Likewise, a receptor polypeptide that is recombinantly produced in substantially pure form contains less 20%, or more preferably 10%, 5%, or 1%, by volume of culture medium. Substantially pure forms of polypeptides may be produced using one or more suitable techniques generally known in the art, such as isolation, purification, peptide synthesis, or recombinant expression. Substantially pure forms of ligand compounds may be prepared using routine chemistry or purification techniques. Substantially pure forms of the complex facilitate their use in applications such as x-ray crystallography to yield a co-crystal structure that may be employed in conformational studies or computational modeling to aid in the design of drugs useful in treating disorders mediated by modulation (e.g., agonism or antagonism) of GPR81 receptor activity or ligand/receptor interaction.

In the ligand-and-receptor complex of the invention, a component, e.g., the ligand, may be optionally labeled with a detectable agent, such as a radio-isotope or a fluorescent molecule. For instance, labeling can be accomplished by replacing one of the atoms of the molecular component with a corresponding radioactive isotope. A hydrogen atom could be replaced with tritium, $^3H$; a carbon atom could be replaced with carbon-14, $^{14}C$, or a strontium atom could be replaced with strontium-38, $^{38}Sr$. In another exemplary labeling process, rather than replacing atoms with a radioactive isotope, an isotope can be added to the molecule. Such radioactive isotopes include, for example, iodine-125, $^{125}I$; and iron-59, $^{59}Fe$.

Any suitable technique described or used in the art to constitute a ligand and receptor complex may be used to form the complex. For example, a sample comprising the ligand component may be mixed with a sample comprising the receptor component.

Since a GPCR binds to its ligand with its extracellular domain, such a binding domain can be identified by various methods known in the art, such as sequence analyses, protein-protein interaction analyses, protein structural analyses, or a combination of these methods. See, e.g., O'Hara et al., 1993, *Neuron*, 11(1): 41-52; David et al., 1999, *J Biol Chem*, 274: 33488-33495. In a preferred embodiment, the ligand binding domain of the GPR81 can be first identified, and such a binding domain can be recombinantly expressed, purified, and used in forming a complex of the invention.

Another general aspect of the invention relates to a method of identifying modulators that either increase or decrease biological activity of the ligand/receptor complex. A biological activity or functional activity of a polypeptide or nucleic acid refers to an activity exerted by a polypeptide or nucleic acid molecule as determined in vivo, or in vitro, according to standard techniques. Such activities can be a direct activity, such as an association with or an enzymatic activity on a second protein, or an indirect activity, such as a cellular signaling activity mediated by interaction of the protein with a second protein.

Modulators of GPR81 biological activity are useful as therapeutic agents in treating a subject suffering from a disease, disorder, or medical condition mediated by GPR81 modulation, for example, diabetes, obesity, hyperlipidemia, lactate acidosis, congestive heart failure, Huntington's disease or disorder, or drug abuse or addiction, metabolic disorders, cancers, central nervous system associated diseases, diseases mediated by one or more growth hormone deficiencies, lactate induced panic attacks, immune disease, and diseases moderated by collagen degradation, such as skin wrinkling and aging.

Modulators are intended to include both inhibitors and activators. Inhibitors are compounds that decrease, prevent, inactivate, desensitize or down-regulate ligand/receptor complex expression or activity, whereas activators are compounds that increase, activate, facilitate, sensitize or up-regulate the complex expression or activity.

The compound identification methods can be performed using conventional laboratory formats or in assays adapted for high throughput. A high-throughput assay format is one that allows easy screening of multiple samples simultaneously, and can include the capacity for robotic manipulation. Another desired feature of high throughput assay is a design that is optimized to reduce reagent usage, or minimize the number of manipulations in order to achieve the analysis desired. Examples of assay formats include 96-well or 384-well plates, levitating droplets, and lab-on-a-chip microchannel chips used for liquid-handling experiments. As miniaturization of plastic molds and liquid-handling devices are advanced, or as improved assay formats or devices are designed, greater numbers of samples may be screened more efficiently using the inventive assays.

Test or candidate compounds for screening can be selected from numerous chemical classes, preferably from classes of organic compounds. Although candidate compounds can be macromolecules, preferably the candidate compounds are small-molecule organic compounds, i.e., those having a molecular weight of greater than 50 and less than 2500. Candidate compounds have one or more functional chemical groups necessary for structural interactions with polypeptides. Preferred candidate compounds have at least an amine, carbonyl, hydroxyl or carboxyl group, preferably at least two such functional groups, and more preferably at least three such functional groups. The candidate compounds can comprise cyclic carbon or heterocyclic structural moieties and/or aromatic or polyaromatic structural moieties substituted with one or more of the above-exemplified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound is preferably a DNA or RNA molecule, although modified nucleic acids having non-natural bonds or subunits are also contemplated.

Candidate compounds may be obtained from a variety of sources, including libraries of synthetic or natural compounds. For example, numerous means are available for random and directed synthesis of a variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid-phase or solution-phase libraries: synthetic library methods requiring deconvolution; the "one-bead one-compound" library method; and synthetic library methods using affinity chromatography selection (see, e.g., Lam (1997), *Anticancer Drug Des.* 12:145). Alternatively, libraries of natural compounds in the form of bacterial, fungal, plant and animal extracts are available or may be routinely produced. Furthermore, libraries of antibodies, mimetibodies, nanobodies, and the like may also provide candidate compounds. Additionally, natural and synthetically produced libraries and compounds can be routinely modified through conventional chemical, physical, and biochemical means.

Further, known pharmacological agents can be subjected to directed or random chemical modifications, such as acylation, alkylation, esterification, amidification, etc., to produce structural analogs. Candidate compounds can be selected randomly or can be based on existing compounds that bind to and/or modulate the function of GPCR activity. Therefore, a source of candidate agents is libraries of molecules based on known activators or inhibitors for GPCRs with similar structures to identified GPR81 ligands, in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions.

A variety of other reagents also can be included in the mixture. These include reagents such as salts, buffers, neutral proteins (e.g., albumin), and detergents that can be used to facilitate optimal protein-protein and/or protein-nucleic acid binding. Such a reagent can also reduce non-specific or background interactions of the reaction components. Other reagents that improve the efficiency of the assay, such as nuclease inhibitors, antimicrobial agents, and the like, can also be used.

Examples of methods for the synthesis of molecular libraries can be found in the art, for example in: Zuckermann et al. (1994), *J Med. Chem.* 37:2678. Libraries of compounds can be presented in solution (e.g., Houghten (1992), *Biotechniques* 13:412-421), or on beads (Lam (1991), *Nature* 354: 82-84), chips (Fodor (1993), *Nature* 364:555-556), bacteria (U.S. Pat. No. 5,223,409), spores (U.S. Pat. No. 5,571,698), plasmids (Cull et al. (1992), *Proc. Natl. Acad. Sci. USA* 89:1865-1869) or phage (see e.g., Scott and Smith (1990), *Science* 249:386-390).

Thus, in another aspect, the invention relates to a method of identifying a compound that increases or decreases a biological activity of a ligand/GPR81 complex, comprising the steps of: (a) contacting a solution comprising a buffer and a candidate or test compound with a assay reagent comprising the ligand and receptor complex; (b) measuring the biological activity of the complex; and comparing the result of step (b) with that of a control wherein the complex was contacted with only the buffer.

As described above, the complex comprises a ligand component and a receptor component. In a preferred embodiment, the complex in the method is associated with a cell expressing the GPR81 on the cell surface (i.e., on the surface of one or more cells).

The cells may be selected as appropriate for the sensitivity of the detection method. Cells suitable for use in the present invention may be bacterial, but are preferably eukaryotic, such as yeast, insect, or mammalian. The cell can be a natural host cell for an endogenous GPR81, preferably a recombinant host cell for a GPR81, which expresses increased amount of a mammalian GPR81 on the cell surface.

In one preferred embodiment, GPR81 is expressed on the cell surface of a GPR81 host cell, preferably a recombinant GPR81 host cell. In another preferred embodiment, GPR81 is associated with isolated cell membranes from a GPR81 host cell, preferably from a recombinant GPR81 host cell. A host cell is a cell that contains a DNA molecule either on a vector or integrated into a cell chromosome. A host cell can be either a native host cell that contains the DNA molecule endogenously, or a recombinant host cell.

The sample comprising the receptor component may comprise, e.g., intact host cells with GPR81 expressed on the cell-surface or isolated cell membranes from host cells of GPR81, or purified GPR81. Although an endogenous host cell for GPR81 receptor can be used, a recombinant host cell expressing an increased amount of GPR81 on the cell surface is preferred.

In a preferred embodiment, the biological activity of the complex can be measured by a second messenger response of the cell. For example, the biological activity of the complex can be measured by the signal transduction event triggered by activated GPR81. This signal transduction event can be measured indirectly by means of measuring one or more changes in cellular physiology, such as cell morphology, migration, or chemotaxis, using one or more suitable methods known to those skilled in the art. It can also be measured directly by measuring phosphorylation of proteins involved in the signal transduction pathway, for example, the phosphorylation of a GTP-binding protein (G protein). Methods are known are available to those skilled in the art to measure protein phosphorylation, for example, by using an ATP or GTP molecule that has been radiolabeled on the γ-phosphate.

The biological activity of the complex may also be measured by the intracellular concentration of a second messenger molecule using any of a number of suitable techniques known to those skilled in the art. For example, the pH change can be measured using a pH sensitive dye, such as Acridine Orange. The calcium concentration can be measured via optical imaging of fluorescent indicators sensitive to $Ca^{2+}$, such as fluo-3 (pentapotassium salt, cell-impermeant form; Molecular Probes) or fluo-3(AM) (an acetoxymethyl ester form of fluo-3, Teflabs) (see for example, Liu et al., 2001, *J Pharmacol Exp Ther.* 299: 121-30) using a fluorometric imaging plate reader (FLIPR) or a confocal microscope (see Example 6). The cAMP concentration can be detected using a commercially available ELISA kit (FLASHPLATE cyclic AMP assay system ($^{125}$I), Cat. No: SMP001A, NEN; see also Shimomura et al., 2002, *J Biol Chem.* 277: 35826-32) (see Example 8), or via a reporter system wherein the expression of a reporter gene, such as beta-galactosidase, is under the control of a cAMP responsive element (cre) (Montminy et al., 1990, *Trends Neurosci*, 13(5): 184-8).

The test compound can be further characterized by comparing its effect on two cells, the first cell containing a functional GPR81 and the second one identical to the first, but lacking a functional GPR81. This technique is also useful in establishing the background noise of these assays. One of ordinary skill in the art will appreciate that this control mechanism also allows ready selection of cellular changes that are responsive to modulation of functional GPR81. Therefore, in a preferred embodiment, the screening method comprises the steps of: (a) contacting a first cell having a GPR81 expressed on the cell surface with a ligand component and with a test compound; (b) determining a second messenger response in the first cell to the test compound, and comparing it with that of a control wherein the first cell is only contacted with the ligand component but not the test compound; (c) contacting a second cell with a ligand component with a test compound; wherein the second cell is otherwise identical to the first cell except that it does not express a GPR81 on the cell surface; (d) determining a second messenger response of the second cell to the test compound, and comparing the second messenger response with that of a control wherein the second cell is only contacted with the ligand component but not the test compound; and (e) comparing the comparison result of step (b) with that of step (d).

There are a number of ways to obtain two cells that are otherwise identical except that one expresses a GPR81 on its cell surface and the other does not. In one embodiment, the first cell is a recombinant host cell for GPR81 that constitutively expresses GPR81 on its cell surface, and the second cell is the parent cell from which the GPR81 recombinant cell is constructed. In another embodiment, a recombinant host cell for GPR81 is constructed such that the expression of GPR81 on the cell surface is under the control of an inducible promoter. The first cell is the recombinant cell grown under inducible conditions that allows the expression of GPR81 on its cell surface, and the second cell is the recombinant cell grown under non-inducible conditions that do not allow the expression of GPR81. In yet another embodiment, the first cell is a native host cell for GPR81 that expresses GPR81 on its cell surface, and the second cell is a mutant cell derived from the native host, wherein the GPR81 gene has been inactivated through mutagenesis. Standard molecular biology methods can be used to construct a recombinant host cell for GPR81, or to inactivate a GPR81 gene.

In another preferred embodiment, the present invention provides a method of identifying a compound that increases or decreases the activity of a ligand/receptor complex, comprising the steps of: (a) contacting an isolated membrane preparation comprising a receptor component with a ligand component, with a test compound, and with a GTP molecule that has been labeled on the γ-phosphate; and (b) determining the amount of labeling bound to the membrane preparation; and (c) comparing the amount of labeling in step (b) with that of a control wherein the membrane preparation is only contacted with the ligand component and the labeled GTP but not the test compound.

The membrane preparation can be isolated from a native host cell that expresses GPR81 on its cell surface, or preferably, from a recombinant host cell that expresses increased amount of GPR81 on its cell surface. It can also be isolated from tissues comprising GPR81 host cells.

A variety of labels can be used to label the GTP molecule on the γ-phosphate, such as a fluorescent molecule or a radioactive isotope such as $^{35}S$, $^{32}P$, and the like.

In yet another embodiment, the present invention provides a method of identifying a compound that binds to a GPR81, comprising the steps of: (a) contacting a receptor component with a test compound, and with a labeled ligand component; (b) measuring the amount of the labeled ligand component that binds to the receptor component; and (c) comparing the measured amount of (b) with that of a control, wherein the GPR81 is only contacted with a labeled ligand component, but not the test compound.

In one preferred embodiment, a GPR81 host cell (recombinant or native) that expresses the GPR81 on the cell surface can be used for the binding assay. In another preferred embodiment, isolated membrane preparations comprising the receptor component can be used for the binding assay. In yet another preferred embodiment, a substantially purified GPR81 receptor component that is capable of binding to L-lactate can be used for the binding assay.

The amount of the ligand component that binds to the receptor component can be measured by first separating the unbound labeled ligand from the receptor, and then measuring the amount of labeling that is associated with the receptor.

Separation of the GPR81 protein from unbound labeled ligand component can be accomplished in a variety of ways. Conveniently, the GPR81 may be immobilized on a solid substrate, from which the unbound ligand can be easily separated. The solid substrate can be made of a variety of materials and in a variety of shapes, e.g., microtiter plate, microbead, dipstick, resin particle, etc. The substrate preferably is chosen to maximize signal-to-noise ratios, primarily to minimize background binding, as well as for ease of separation and cost.

Separation can be effected by, for example, removing a bead or dipstick from a reservoir, emptying or diluting a reservoir such as a microtiter plate well, or rinsing a bead, particle, chromatographic column or filter with a wash solution or solvent. The separation step preferably includes multiple rinses or washes. For example, when the solid substrate is a microtiter plate, the wells can be washed several times with a washing solution, e.g., that includes those components of the incubation mixture that do not participate in specific bindings, such as salts, buffer, detergent, non-specific protein, etc. Where the solid substrate is a magnetic bead, the beads can be washed one or more times with a washing solution and isolated using a magnet.

GPR81 may be immobilized on a solid substrate using a number of methods. For example, a fusion protein may be provided which adds a domain that allows the GPR81 protein to be bound to a matrix. For example, glutathione-S-transferase fusion proteins or glutathione-S-transferase fusion proteins can be adsorbed onto glutathione sepharose beads (Sigma Chemical, St. Louis, Mo.) or glutathione derivatized microtiter plates, which are then combined with the test compound and the labeled ligand, and the mixture is incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes may be dissociated from the matrix, and the level of binding or the labeled ligand to receptor can be determined using standard techniques.

Other techniques for immobilizing proteins on matrices can also be used in the screening assays of the invention. For example, the GPR81 may be immobilized utilizing conjugation of biotin and streptavidin. Biotinylated polypeptide can be prepared from biotin-NHS (N-hydroxy-succinimide) using techniques known in the art (e.g., biotinylation kit available from Pierce Chemicals, Rockford, Ill.), and immobilized in the wells of streptavidin-coated 96-well plates (Pierce Chemicals).

Alternatively, antibodies reactive with the GPR81 but which do not interfere with binding of it to ligand or test compound can be attached to the wells of the plate, and GPR81 then trapped in the wells by antibody conjugation.

A variety of labels can be used to label the ligand, such as those that provide direct detection (e.g., radioactivity, luminescence, optical or electron density, etc), or indirect detection (e.g., epitope tag such as the FLAG epitope, enzyme tag such as horseradish peroxidase, etc.).

Interaction of the receptor component to ligand component in the presence and absence of a candidate compound can be accomplished in any vessel suitable for containing the reactants. Examples of such vessels include microtiter plates, test tubes, and micro-centrifuge tubes.

In another general aspect, the invention relates to a method for identifying a compound that binds GPR81 and mimics L-lactate, comprising the steps of: (a) contacting a test compound with an assay reagent comprising a receptor component; (b) measuring a biological activity of the receptor component; and comparing the result of step (b) with that of a control wherein the receptor component was contacted with the ligand component in the absence of the test compound.

In one preferred embodiment of this method, the GPR81 receptor component is expressed from a recombinant cell, preferably on the cell surface. In another preferred embodiment, the receptor component is within an isolated cell membrane preparation.

The biological activity can be any of the biological activities associated with the receptor-and-ligand complex or the interaction of GPR81 and L-lactate, such as the signal transduction event or the changes in intracellular concentration of a second messenger molecule triggered by activated GPR81. These biological activities can be measured using any suitable method such as one discussed herein. A test compound that mimics L-lactate elicits a similar change in the biological activity of GPR81 as that of L-lactate.

Accordingly, a therapeutically effective amount of a test compound that modulates GPR81 activity may be administered to a subject suffering from or diagnosed with a disease, disorder, or medical condition associated with the biological activity induced by the ligand-receptor binding, such as overactivity or insufficient activity of GPR81. The term "subject" refers to an animal patient. Preferably, the subject is a mammal, more preferably a human. The term "therapeutically effective amount" as used herein means that amount of the compound that elicits the desired biological or medicinal response in a tissue system, animal or human that is being sought by a researcher, veterinarian, medical doctor or other clinician, such as alleviation of the symptoms of the disease or disorder being treated. Methods are known in the art for routinely determining therapeutically effective doses for pharmaceutical compositions.

L-Lactate as Ligand for GPR81

As an effort to de-orphanize GPR81, different rat tissues were extracted and applied to cell membranes recombinantly expressing GPR81. It was found that those tissue extracts contain a substance (ligand) that specifically stimulates $^{35}$S-GTPγS incorporation for GPR81 expressing cells but not the control cells. Biochemical purification guided by functional assay for the GPR81 ligand activity indicated that the active ligand is lactate. Functional assay using pure L-lactate from a commercial source confirmed that L-lactate is indeed an agonistic ligand for GPR81.

L-lactate is a normal product in human and animals from anaerobic oxidation of glucose. For a long time lactate had been regarded as a by-product or a waste of metabolism because, in the metabolic system, lactate is the dead end of metabolism. However, lactate can be converted back to pyruvate or glucose by many tissues or cells. Recent researches suggest that lactate is not a waste of the body metabolism— instead, lactate may serve as a metabolism stimulator and a fast fuel for organs (such as muscle cells or neurons) or tissues that need immediate energy. Some cells such as neurons actually prefer using lactate to glucose. The physiological concentration of lactate in human blood is about 1 mM and the concentration of L-lactate in tissues ranging from 10 to 20 mmol/kg. During exercise, lactate concentration in blood may increase up to 10 to 20 mM. In vitro pharmacology shows that L-lactate activates GPR81 with an $EC_{50}$ value of 5 mM. L-lactate, at 1 mM concentration, is capable of stimulating detectable receptor activation. The results described in more detail below demonstrate that the pharmacology of L-lactate/GPR81 fits the dynamic range of L-lactate concentrations in blood, reflecting that GPR81 plays a role in sensing the L-lactate concentration and body metabolism.

Thus, in preferred embodiments of the ligand-and-receptor complex of the invention, the ligand component is L-lactate or a mimetic thereof. A mimetic is a compound that is chemically similar to L-lactate and elicits a similar change in the biological activity of GPR81. Exemplary L-lactate mimics are the GPR81 agonists are described in the following examples.

The examples below are provided to further illustrate various features and embodiments of the invention.

EXAMPLES

Materials and Methods
Molecular Cloning of GPR81.

The human GPR81 coding region was identified from the human genome draft sequence using human histamine H4 receptor as the query. Two primers (forward primer: 5' ACT GGA ATT CGC CAC CAT GTA CAA CGG GTC GTG CTG CCG C3' (SEQ ID NO:1)); and reverse primer: 5' ACG TCA GCG GCC GCT CAG TGC CAC TCA ACA ATG TGG GGA T 3' (SEQ ID NO:2)) were designed according to the predicted coding region of the human GPR81 gene and used to PCR amplify the full coding region using the human genomic DNA as the template. PCR was performed for 35 cycles at the following conditions: 94° C. for 20 seconds, 65° C. for 30 seconds, and 72° C. for 3 minutes, using the Expanded High Fidelity PCR system (Roche Bioscience). The PCR product was cloned into a mammalian expression vector pCIneo (Promega) and the insert region was confirmed by DNA sequencing (Eton Biosciences, San Diego) (See FIG. 1 and SEQ ID NO:31).

The rat GPR81 coding region was identified from the rat genomic sequence using the human GPR81 sequence as the query. Two potential translation sites for rat GPR81 were identified; the 3' translation start site matched the human GPR81 translation start site. The rat GPR81 polypeptide sequence predicted to be expressed from the 5' translation start site is eight amino acids longer than the rat GPR81 polypeptide sequence predicted to be expressed from the 3' translation start site. The longer polypeptide sequence was termed rat GPR81L; the shorter polypeptide sequence was termed rat GPR81S. The cDNAs encoding rat GPR81L and rat GPR81S were each PCR amplified, respectively, using rat genomic DNA as the template. The forward primer, 5' AGT CAC GAA TTC. GCC ACC ATG CTC TTC CTC TCT CCG AGT GCT ATG 3' (SEQ ID NO:7), and the reverse primer, 5' ACT AGA GCG GCC GCT CAA CAC ACT TGG AGA CCC CAC TG 3' (SEQ ID NO:8) were used to amplify rat GPR81L. The forward primer, 5' AGT CAC GAA TTC GCC ACC ATG GAC AAC GGG TCG TGC TGT CTC A 3' (SEQ ID NO:9), and reverse primer, 5'ACT AGA GCG GCC GCT CAA CAC ACT TGG AGA CCC CAC TG 3' (SEQ ID NO:10), were used to amplify rat GPR81S. The PCR conditions were the same as those used to amplify human GPR81. The PCR products were cloned into the mammalian expression vector, pCIneo, and the insert regions were sequenced to confirm their identities (for rat GPR81L, see FIG. 2 and SEQ ID NO:33; for rat GPR81S, see FIG. 3 and SEQ ID NO:37).

The mouse GPR81 coding region was identified from the mouse genomic sequence using the human GPR81 sequence as the query. Two potential translation sites for mouse GPR81 were identified; the 3' translation start site matched the human GPR81 translation start site. The mouse GPR81 polypeptide sequence expressed from the 5' translation start site was predicted to be eight amino acids longer than the mouse GPR81 polypeptide expressed from the 3' translation start site. The longer polypeptide sequence was termed mouse GPR81L; the shorter polypeptide sequence was termed mouse GPR81S. The cDNAs encoding mouse GPR81L and mouse GPR81S were each PCR amplified, respectively, using mouse genomic DNA as the template. The forward primer, 5' AGT CAC GAA TTC GCC ACC ATG CCA GTC CTC TCT CCA ACT GCT ATG 3' (SEQ ID NO:3), and the reverse primer, 5' ACT AGA GCG GCC GCT CAA CAC ACT TGG AGA TCC CAC TG 3' (SEQ ID NO:4), were used to amplify mouse GPR81L. The forward primer, 5' AGT CAC GAA TTC GCC ACC ATG GAC AAC GGG TCG TGC TGT CTC A 3'(SEQ ID NO:5), and the reverse primer, 5' ACT AGA GCG GCC GCT CAA CAC ACT TGG AGA TCC CAC TG 3' (SEQ ID NO:6), were used to amplify mouse GPR81S. The PCR conditions were the same as those used to amplify human GPR81. The PCR products were cloned into the mammalian expression vector, pCIneo, and the insert regions were sequenced to confirm their identities (for mouse GPR81L, see FIG. 4 and SEQ ID NO:35; for mouse GPR81S, see FIG. 6 and SEQ ID NO:39).

The bovine GPR81 coding region was identified from the bovine genomic sequence by searching the NCBI database using the human GPR81 boding region as the query. The forward primer, 5' ATG ACA GAA TTC GCC ACC ATG GCC AAC AGG TCG TGC TGT CTC ATC 3' (SEQ ID NO:11), and the reverse primer, 5' ACT AGA GCG GCC GCC ATG GAG TAT ITC TAA GTC ACC AAT CC 3' (SEQ ID NO:12), were designed based on the identified bovine GPR81 coding sequence and were used to amplify the bovine GPR81 coding region using bovine genomic DNA as template. The PCR conditions were the same as those used to amplify human GPR81. The PCR product was cloned into the mammalian expression vector, pCIneo, and the insert region was sequenced to confirm its identity (See FIG. 6 and SEQ ID NO:41).

The dog GPR81 coding region was identified from the dog genomic sequence by searching the NCBI database using the human GPR81 coding region as the query. The forward primer, 5' ACT AGA GAA TTC GCC ACC ATG GAC AAC GGG TCG TGC TGC CTC ATC 3' (SEQ ID NO:13), and the reverse primer, 5' ACT AGA GCG GCC GCG AGG AGG ATA CAG CTG AGG AAG GGT G 3' (SEQ ID NO:14), were designed based on the identified dog GPR81 coding sequence and were used to amplify the dog GPR81 coding region using dog genomic DNA as template. The PCR conditions were the same as those used to amplify human GPR81. The PCR product was cloned into the mammalian expression vector, pCIneo, and the insert region was sequenced to confirm its identity (See FIG. 7 and SEQ ID NO:43).

The monkey GPR81 coding region was identified from the monkey genomic sequence by searching the NCBI database using the human GPR81 coding region as the query. The forward primer, 5' ACT AGA GAA TTC GCC ACC ATG TAC AAC GGG TCG TGC TGC CGC AT 3' (SEQ ID NO:15), and the reverse primer, 5' ATG ATA GCG GCC GCT CAG TGC CAC TCA ACA GTG TGG GGA TC 3' (SEQ ID NO:16), were designed based on the identified monkey GPR81 coding sequence and were used to amplify the monkey GPR81 coding region using monkey genomic DNA as template. The PCR conditions were the same as those used to amplify human GPR81. The PCR product was cloned into the mammalian expression vector, pCIneo, and the insert region was sequenced to confirm its identity (See FIG. 8 and SEQ ID NO:45).

The porcine GPR81 coding region was identified from the porcine genomic sequence by searching the NCBI database using the porcine GPR81 coding region as the query. The forward primer, 5' ACT GAG GAA TTC GCC ACC ATG GAC AAC GGG TCA TGC TGC CTC ATC 3' (SEQ ID NO:17), and the reverse primer, 5' ACT GAG GCG GCC GCT GTC TGT CCA TCA ATT CTG ATG CCA TC 3'(SEQ ID NO:18), were designed based on the identified porcine GPR81 coding sequence and were used to amplify the porcine GPR81 coding region using porcine genomic DNA as template. The PCR conditions were the same as those used to amplify human GPR81. The PCR product was cloned into the mammalian expression vector, pCIneo, and the insert region was sequenced to confirm its identity (See FIG. 9 and SEQ ID NO:47).

Detection of GPR81 mRNA Expression in Different Tissues from Human, Rat, and Mouse.

The following PCR primer pairs were designed according to human, rat, and mouse GPR81 cDNA sequences, respectively:

```
Human forward:
5' TGCCCAGCGTGTCTGCTAGACT 3';        (SEQ ID NO: 19)

Human reverse:
5' TACACCAGGGGATCCAGCATGC 3';        (SEQ ID NO: 20)

Rat forward:
5' GAGTTGTTTGGAGCCTGAGACAGA 3';      (SEQ ID NO: 21)

Rat reverse:
5' GGGGCTTGAGAAGTAGTACAC 3';         (SEQ ID NO: 22)

Mouse forward:
5' CCGGTTCATCATGGTGGTGGCT 3';        (SEQ ID NO: 23)
and

Mouse reverse:
5' CTCTTCTGACCTCCGCGTCTTC 3'.        (SEQ ID NO: 24)
```

In addition, the following β-actin primer pairs were designed according to the human, rat, and mouse β-actin cDNA sequences, respectively:

```
Human forward:
5' GGTCATCACCATTGGCAATGAG 3';        (SEQ ID NO: 25)

Human reverse:
5' GATCTTGATCTTCATTGTGCTG 3';        (SEQ ID NO: 26)

Rat forward:
5' CAACACAGTGCTGTCTGGTG 3';          (SEQ ID NO: 27)

Rat reverse:
5' GATCCACATCTGCTGGAAG 3';           (SEQ ID NO: 28)

Mouse forward:
5' ACAACGGCTCCGGCATGTGCA 3';         (SEQ ID NO: 29)
and

Mouse reverse:
5' GTGTGGTGCCAGATCTTCTCCA 3'.        (SEQ ID NO: 30)
```

GPR81 and β-actin mRNA expression was analyzed using quantitative PCR as described previously (Liu et al., *J. Biol. Chem.*, Vol. 280, pp. 292-300 (2005); relative abundance of GPR81 mRNA was expressed as a ratio over β-actin.

Expression of GPR81 Constructs in Mammalian Cells.

The GPR81 cDNA-pCIneo constructs described above were each transiently transfected into CHO-K1 cells (ATCC) using LipofectAmine (Invitrogen) as the transfection reagent, as described by the manufacturer. Two days after transfection, cell culture medium was aspirated and cells were scraped into PBS plus 10 mM EDTA. Cell pellets were collected by centrifugation at 10,000×g for 10 minutes at 4° C. and stored at −80° C. until further use.

GTPγS Binding Assays.

GTPγS binding assays were performed as previously described (Liu et al., *J. Biol. Chem.*, Vol. 278, pp. 50754-50764 (2003)). Cell membranes were prepared from cells expressing GPR81 cDNA as described above. The membranes were dissolved in GTPγS binding buffer (50 mM Tris-HCl pH 7.5, 100 mM NaCl, 10 mM MgCl$_2$, 1 mM EDTA and 1% BSA) then aliquoted into 96-well plates. Tissue extracts at indicated dilutions were applied to cell membranes and incubated at room temperature for 20 minutes. Aliquots of $^{35}$S-GTPγS were added to samples to a final concentration of 1 nM, and the samples were then incubated at room temperature for an additional hour. Samples were then filtered through a 96-well GFC plate (Packard), and the bound $^{35}$S-GTPγS was counted in a top counter (TopCount NTX, Packard). Cell membranes from cells not expressing GPR81 were used as negative controls in parallel experiments.

Identification of Ligand Activity from Rat Tissue Extracts.

Rat tissues (5 g/per tissue) were homogenized in cold ethanol (80%) at a tissue solvent ratio of 1:8. The tissues were extracted at 4° C. for four hours, and then centrifuged at 10,000×g for 30 minutes. The supernatants were collected, and ethanol was evaporated from samples using a Rotavap with vacuum at 30° C. The remaining solution was centrifuged at 10,000×g for 30 minutes at 4° C. The resulting supernatant was passed through a C-18 SPE column (Bond Elut, Variant), and the flow-through was collected and dried in a lyophilizer. The dried sample was re-extracted with pure ethanol, and the supernatant was dried in the Rotavap and reconstituted in water. Reconstituted samples were then tested for GPR81 ligand activity in the GTPγS binding assay employing cell membranes expressing the human GPR81.

Purification and Identification of the Ligand of GPR81 from Porcine Brain.

Approximately 200 grams of frozen porcine brain were homogenized in 1.6 liters of cold solvent (80% ethanol:20% water). The tissue extract was stirred at 4° C. for five hours and centrifuged at 10,000×g for 30 minutes. The supernatant was collected and its volume reduced to approximately 200 mL using a Rotavap at 30° C. The sample was again centrifuged at 10,000×g for 30 minutes, and the supernatant was loaded onto a C-18 column (Varian). The flow-through portion was dried in a lyophilizer in four tubes, resulting in ~500 mg/tube of solid material. Half of the lyophilized material was dissolved in 2 mL distilled water and pH-adjusted to 3 with concentrated HCl before loading onto a Restek AllureOA column (300×10 mm, 5 um, 60 Å). Preparative HPLC was run using a Waters Alliance 2790 system (Flow rate: 4 ml/min, mobile phase: 1 mM HCl in water). Fractions were collected at 0.5 minutes per tube, which were neutralized with NaOH before being tested in a GTPγS binding assay to identify active fractions. Active fractions were lyophilized and dissolved in 0.5 ml D$_2$O. The pH of the sample was adjusted to 8 with NaOD, and NMR data was acquired on a Bruker DRX600 spectrometer at 40° C. ($^1$H, $^{13}$C APT, COSY, HSQC). NMR data was also obtained for a sample containing 15 mg pure (L-) sodium lactate purchased from Sigma under the same conditions.

Pharmacological Characterization of L-lactate and L-lactate-Related Compounds as Ligands for GPR81.

CHO cells transiently expressing human, rat, mouse, bovine, dog, monkey, or porcine GPR81 as described above were used to assay L-lactate, D-lactate and other compounds as indicated for agonist or antagonist activity. In agonist assays, compounds were assayed for the ability to stimulate $^{35}$S-GTPγS incorporation into cell membranes expressing GPR81. In antagonist assays, compounds were used to inhibit L-lactate-induced $^{35}$S-GTPγS incorporation.

A β-galactosidase (β-gal) assay system was also used to characterize the GPR81 activation in SK-N-MC/CRE-β-gal cells stably expressing human GPR81. GPCRs that couple with Gi proteins, upon activation by agonist, inhibit cAMP accumulation, and therefore inhibit forkolin-stimulated β-gal expression. A cell line stably expressing human GPR81 was established from an SK-N-MC/CRE-β-gal cell line, which harbors a β-galactosidase β-gal) gene under the control of a cAMP-responsive element (CRE). SK-N-MC/CRE-β-gal cells were transfected with the above-described human GPR81-pCIneo construct using LipofectAmine as the transfection reagent. Two days after transfection, the cells were split into new culture dishes at different densities and grown under selection of G418 for three weeks. Single isolated clones were isolated and tested for responsiveness to L-lactate stimulation. Responsive cells were grown in 96-well plates and stimulated with 5 μM of forskolin, which stimulates cAMP and induces β-gal expression, in the presence of the various concentrations of L-lactate or nicotinic acid, as indicated. The β-gal activity was assayed as described (Liu et al., Mol. Pharmacol., Vol. 67, pp. 231-240 (2005)).

Results

Identification and Molecular Cloning of GPR81.

The human GPR81 coding region was initially identified from the human genome draft sequence using the human histamine H4 as the query. The Tblastn search revealed a new sequence in the human genome distantly related to human histamine H4 receptor, designated GPR81. Molecular cloning of the human GPR81 from both genomic DNA and cDNA from liver followed by DNA sequencing revealed that GPR81 locus comprises an intronless gene with a coding region of 1041 base pairs and codes for 346 amino acids (FIGS. 1 and 10). A GenBank search showed that human GPR81 is identical to a published orphan GPCR, termed GPR81, and shares about 70% homology to the nicotinic acid receptors, HM74 and HM74A.

The mouse and rat GPR81 genes were identified from the mouse and rat genomic sequence from GenBank, respectively. Compared to human GPR81, in addition to the putative translation initiation site (ATG) corresponding to the human GPR81 translation initiation site, both mouse and rat GPR81 have an additional in frame ATG codon 24 bp upstream which encodes 8 additional amino acids (see FIGS. 2-5 and 10). The mouse and rat GPR81 were cloned from both genomic DNA and cDNA. DNA sequencing results show that, similar to human GPR81, both the mouse and rat GPR81 loci comprise intronless genes. DNA sequence comparison revealed that both mouse and rat GPR81 share about 80% sequence identity to human GPR81 at the DNA and protein levels (see e.g., FIG. 10).

Expression Profile of GPR81 in Different Tissues.

Figure 12:
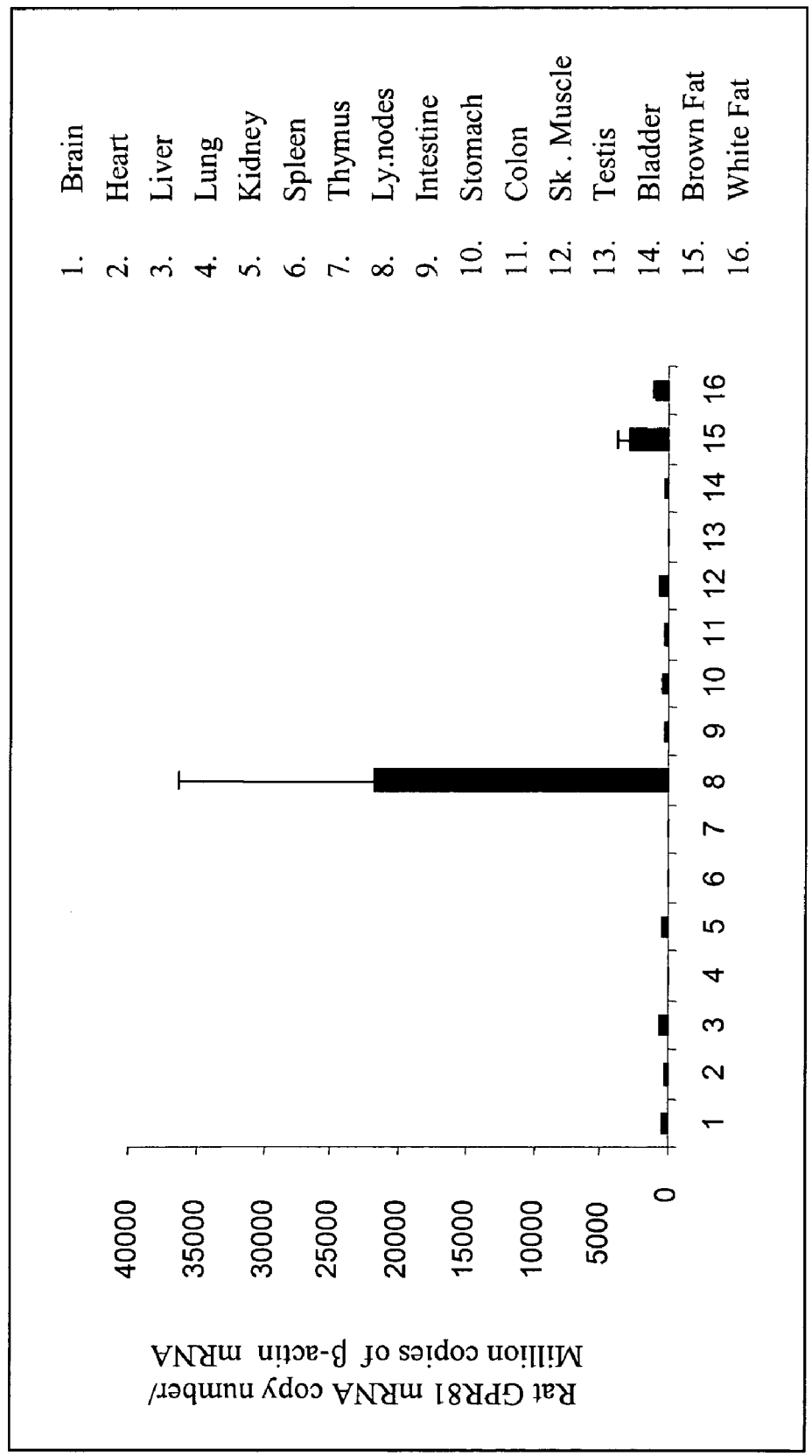
FIG. 12 illustrates the expression levels of rat GPR81 mRNA in the indicated tissues, as determined by quantitative PCR.
Figure 13:
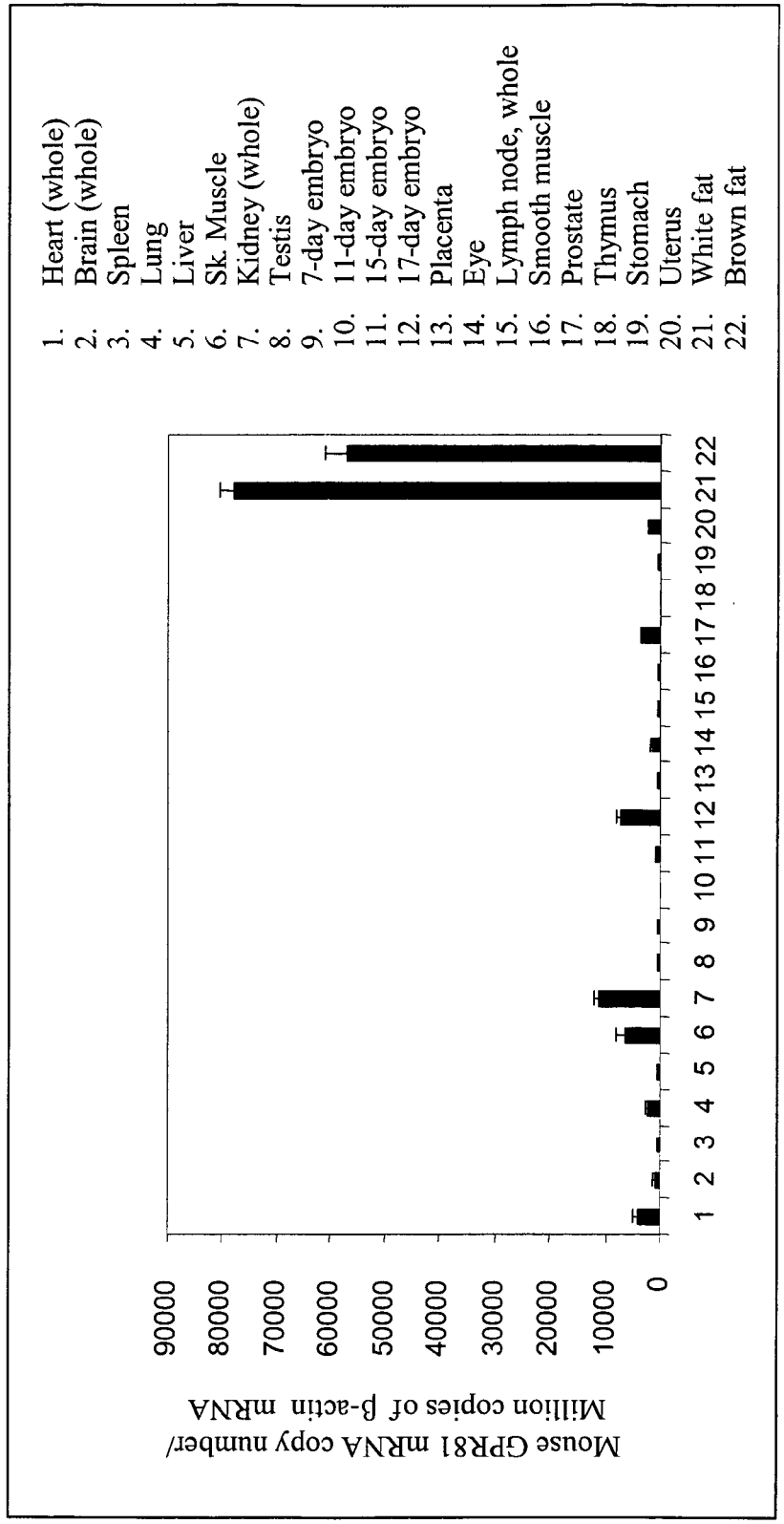
FIG. 13 depicts the expression levels of mouse GPR81 mRNA in the indicated tissues, as determined by quantitative PCR.

GPR81 cDNAs were generated from GPR81 mRNA and amplified via quantitative PCR from the indicated human, rat, and mouse tissues using species-specific primer pairs. As internal controls, species-specific primer pairs for human, rat, and mouse β-actin were used to amplify β-actin cDNA from the same tissue samples. The relative number of GPR81 mRNA copies present in the tissue samples was then normalized to β-actin mRNA copy numbers from the same tissue samples. The results showed that human GPR81 was most abundantly expressed, among the tissues assayed, in brown fat as well as testis, highly expressed (greater than approximately 80 copies GPCR mRNA per million copies β-actin) in white fat, liver, kidney, and skeletal muscle, and expressed at detectable levels in heart, brain, lung, kidney, thymus, prostate, and other tissues (FIG. 11). In rat, GPR81 was found to be most abundantly expressed, among the tissues assayed, in lymph nodes, highly expressed (greater than approximately 800 copies GPR81 mRNA per million copies β-actin) in brown fat, white fat, and liver, and expressed at detectable levels in brain, kidney, stomach, skeletal muscle, and other tissues (FIG. 12). In mouse, GPR81 was found to be most abundantly expressed, among the tissues assayed, in white fat and brown fat, highly expressed (greater than approximately 4000 copies GPCR mRNA per million copies β-actin) in heart (whole), skeletal muscle, kidney (whole), prostate, and 17-day embryonic tissue, and expressed at detectable levels in lung, eye, uterus, and other tissues (FIG. 13).

Detection of Agonist Ligand Activity for GPR81 from Different Rat Tissue Extracts.

Figure 14A:
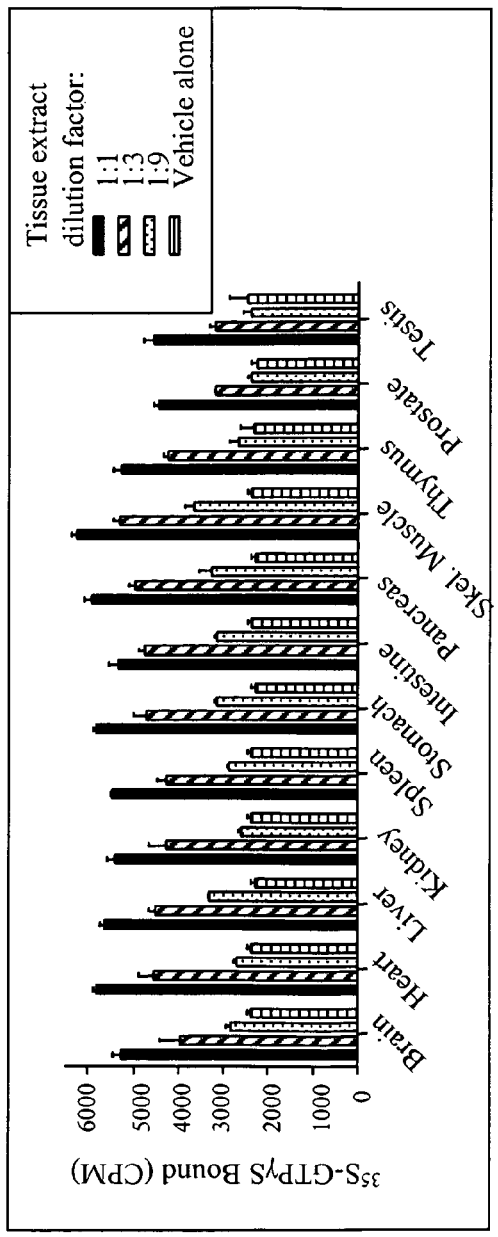
FIGS. 14A and 14B illustrate the results of $^{35}$S-GTPγS binding assays using the indicated dilutions of the indicated tissue extracts to stimulate binding of $^{35}$S-GTPγS to GPR81-expressing membranes (FIG. 14A) or membranes not expressing any GPCR (FIG. 14B).
Figure 14B:
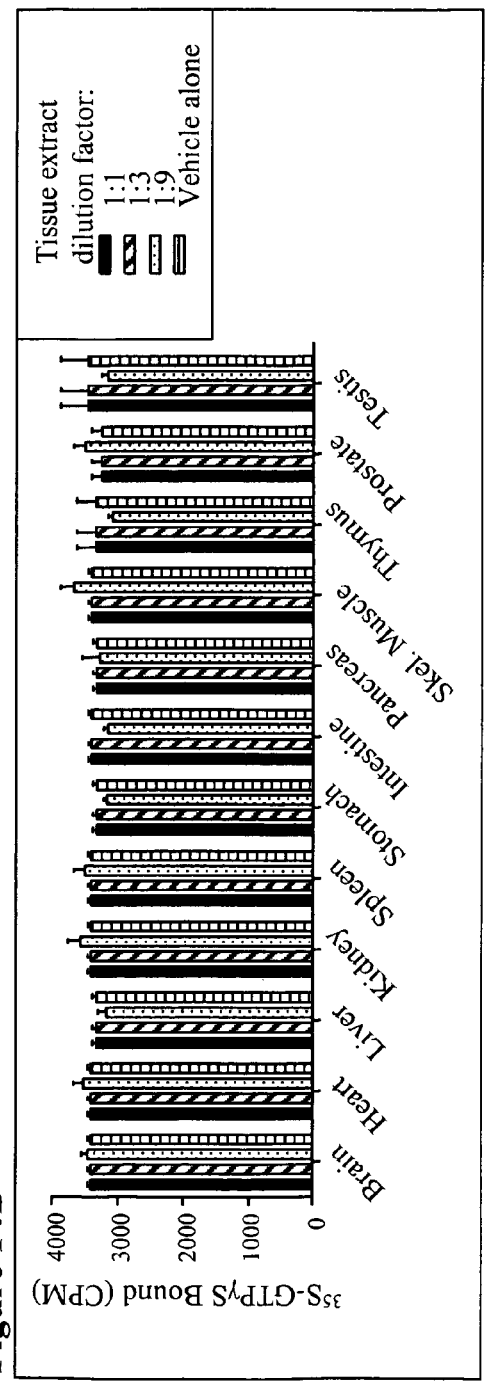

The indicated rat tissue crude extracts were prepared as described above, diluted in water at the indicated dilution factors, and applied to Chinese hamster ovary (CHO) cell membranes expressing human GPR81. The cell membranes were then assayed for the ability of the diluted tissue extracts to stimulate $^{35}$S-GTPγS binding to the membranes. The results, depicted in FIG. 14A, revealed that all the tissue extracts stimulated significant $^{35}$S-GTPγS binding to cell membranes prepared from human GPR81-expressing CHO cells at the 1:1 and 1:3 dilution factors (compared to vehicle alone), and most of the tissue extracts stimulated significant $^{35}$S-GTPγS binding at the 1:9 dilution (relative to vehicle alone). The highest activities were observed in tissue extracts coming from the skeletal muscle, heart, pancreas, stomach and the brain. None of the tissue extracts stimulated significant $^{35}$S-GTPγS binding to cell membranes prepared from control CHO cells, which did not express GPR81 (FIG. 14B). The same tissue extracts were also applied to membrane preparations from 50 different GPCR-transfected CHO cell populations, each population expressing a different GPCR. No apparent $^{35}$S-GTPγS binding was stimulated upon application of any of the tissue extracts to any of the 50 different orphan GPRC-expressing cell membrane preparations. Collectively, these results indicate that agonist ligand activity specific for GPR81 was present in the tissue extracts.

Purification and Identification a Natural Ligand for GPR81 from Porcine Brain.

Figure 15A:
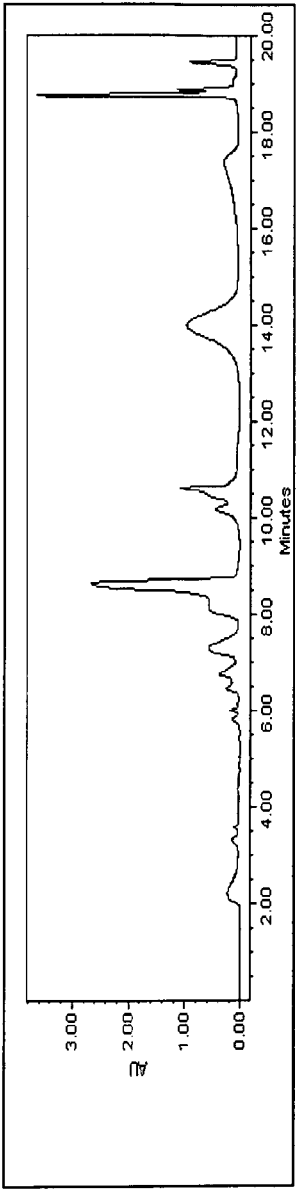
FIGS. 15A-15C depict the isolation of a GPR81 agonist ligand activity from a porcine brain extract.
Figure 15B:
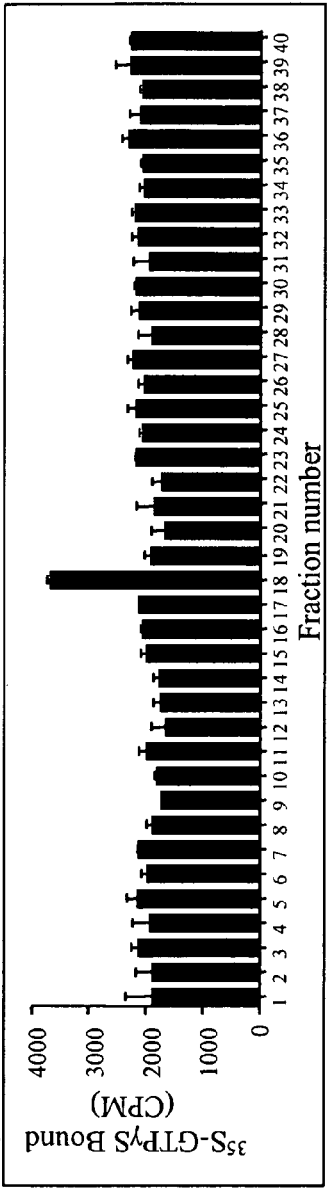
Figure 15C:
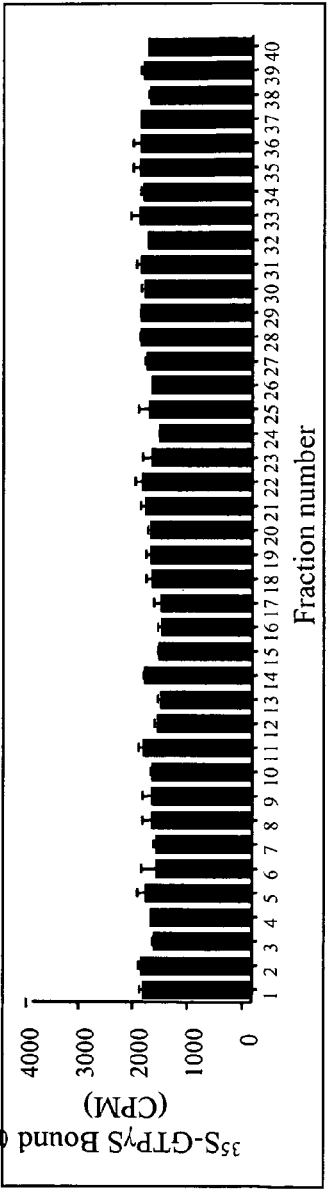
Figure 16:
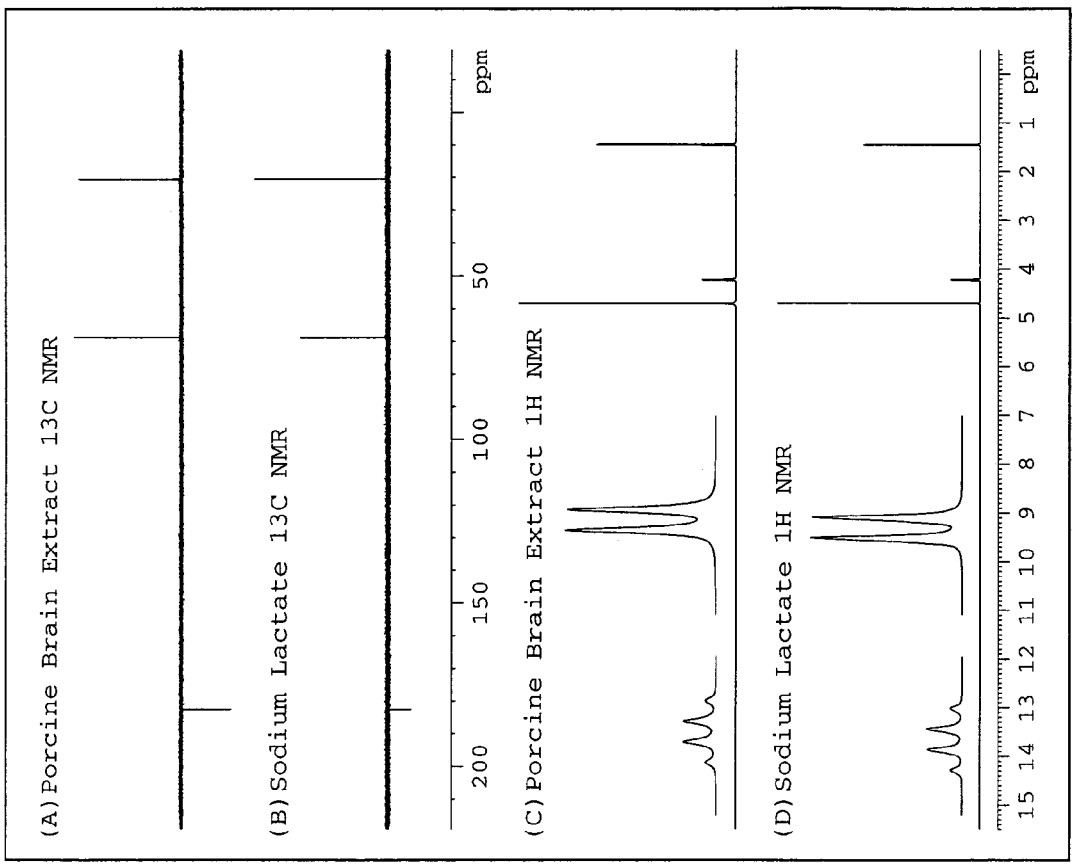
FIG. 16 provides NMR results of the active preparative HPLC fraction, reflecting that L-lactate is the ligand for GPR81.

To purify a ligand for GPR81, approximately 200 grams of porcine brain was subjected to the above-described extraction. A small aliquot of the porcine brain extract was prepared and tested for ligand activity as described above for rat tissue extracts and human GPR81-expressing CHO cells. GPR81 agonist activity was detected in porcine brain extract aliquot. The remaining portion of the porcine brain extract was lyophilized, redissolved in 1 mM HCl, subjected to preparative HPLC, and fractionated with a Restek AllureOA column, as described above. Agonist activity for GPR81 was detected in fraction #18 via the $^{35}$S-GTPγS binding assay, employed as described above (FIGS. 15A-C). The remainder of the fraction #18 was then subjected to $^1$H-NMR and $^{13}$C-NMR as described above, and the data acquired was compared to $^1$H NMR and $^{13}$C NMR data acquired from commercially-obtained L-lactate Sigma. The results, depicted in FIG. 16, show that the $^1$H-NMR and $^{13}$C-NMR spectra obtained from fraction #18 were essentially identical to the $^1$H-NMR and $^{13}$C-NMR spectra obtained from the commercial sodium L-lactate, respectively (FIG. 16, compare spectrum (A) with spectrum (B), and spectrum (C) with spectrum (D)), indicating that the GPR81 agonist component in fraction #18 was L-lactate. This determination was supported by results obtained from COSY and HSQC experiments. The purity of active component in fraction #18, determined to be L-lactate, was over 98% based on both the $^1$H- and $^{13}$C-NMR data (FIG. 16).

Figure 17:
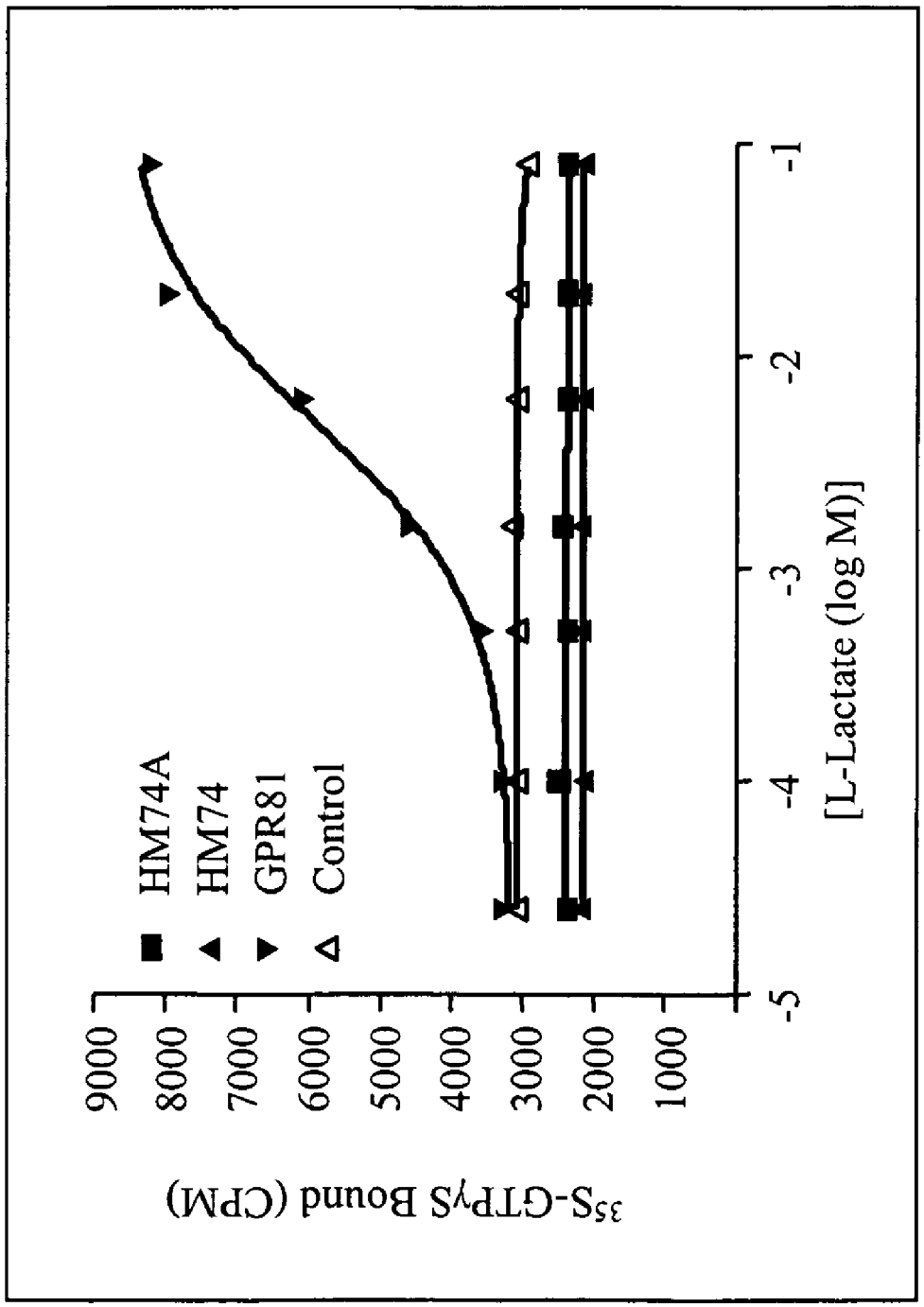
FIG. 17 illustrates the results from testing control cells or cells expressing GPR81, HM74, HM74A with different concentrations of L-lactate in GTPγS binding assays.
Figure 18B:
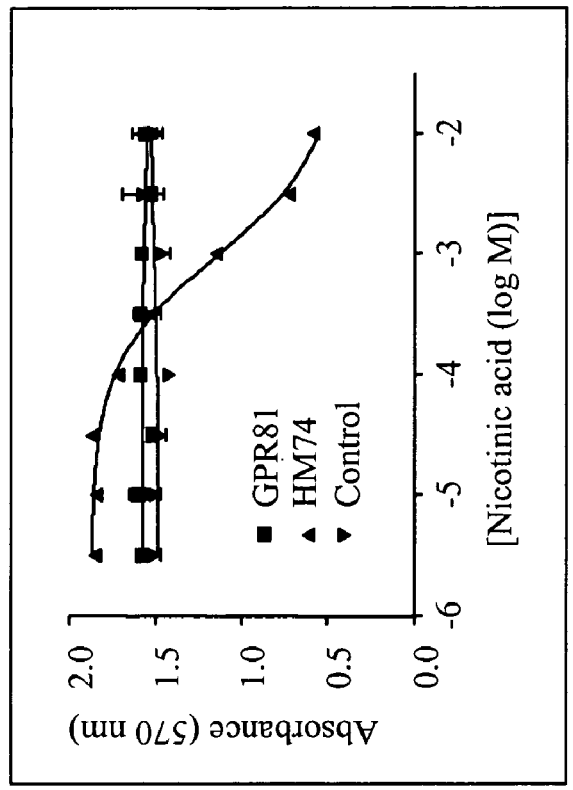
FIG. 18B depicts that nicotinic acid inhibits forskolin-induced β-galactosidase expression in HM74A-expressing cells, but not in cells expressing GPR81.
Figure 18A:
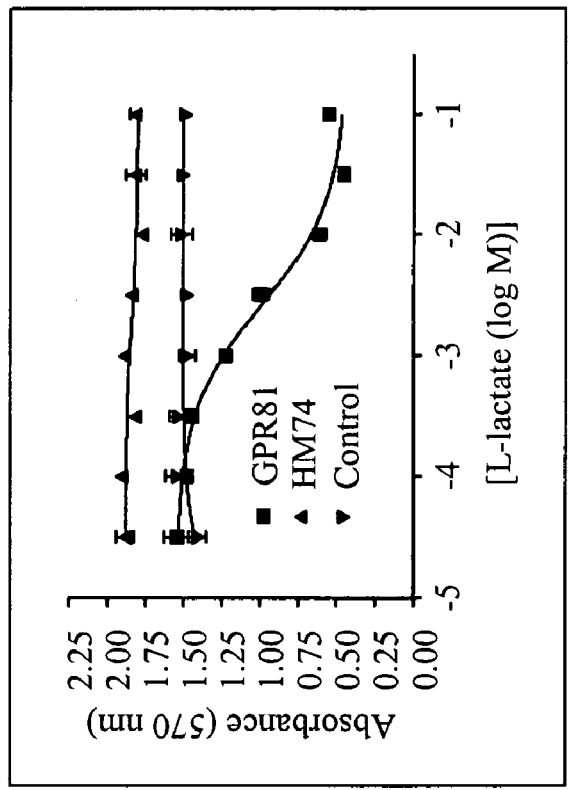
FIG. 18A illustrates that lactate inhibits forskolin-induced β-galactosidase expression, which reflects the intracellular cAMP level, but not in cells not expressing GPR81.

To further characterize the agonist ligand activity of L-lactate for GPR81, commercial L-lactate at various concentrations was tested for activation of GPR81 using GTPγS binding assays and cAMP inhibition-linked β-gal assays, as described above. The $^{35}$S-GTPγS binding assay results showed that, whereas L-lactate did not activate HM74A- or HM74-expressing membranes prepared form CHO cells, or membranes prepared from control CHO cells not expressing any GPCR, L-lactate did activate human GPR81 in a dose-dependent manner with an $EC_{50}$ value of approximately 5 mM (FIG. 17). The cAMP inhibition-linked β-gal assay showed that, whereas that L-lactate did not inhibit forskolin-induced β-gal expression in HM74 expressing cells or control cells not expressing a GPCR, L-lactate did inhibit forskolin-induced β-gal expression in GPR81-expressing cells with an $EC_{50}$ value of approximately 3 mM (FIG. 18A). Furthermore, whereas the HM74 agonist, nicotinic acid, inhibited forskolin-induced β-gal expression in HM74 expressing cells, but failed to inhibit forskolin-induced β-gal expression in GPR81-expressing cells or in control cells not expressing a GPCR (FIG. 18B). Collectively, these results suggest that L-lactate is a natural and selective agonist ligand for GPR81.

Characterization of L-lactate and Related Compound Agonist Ligand Activity Toward GPR81 from Other Mammalian Species.

Figure 19:
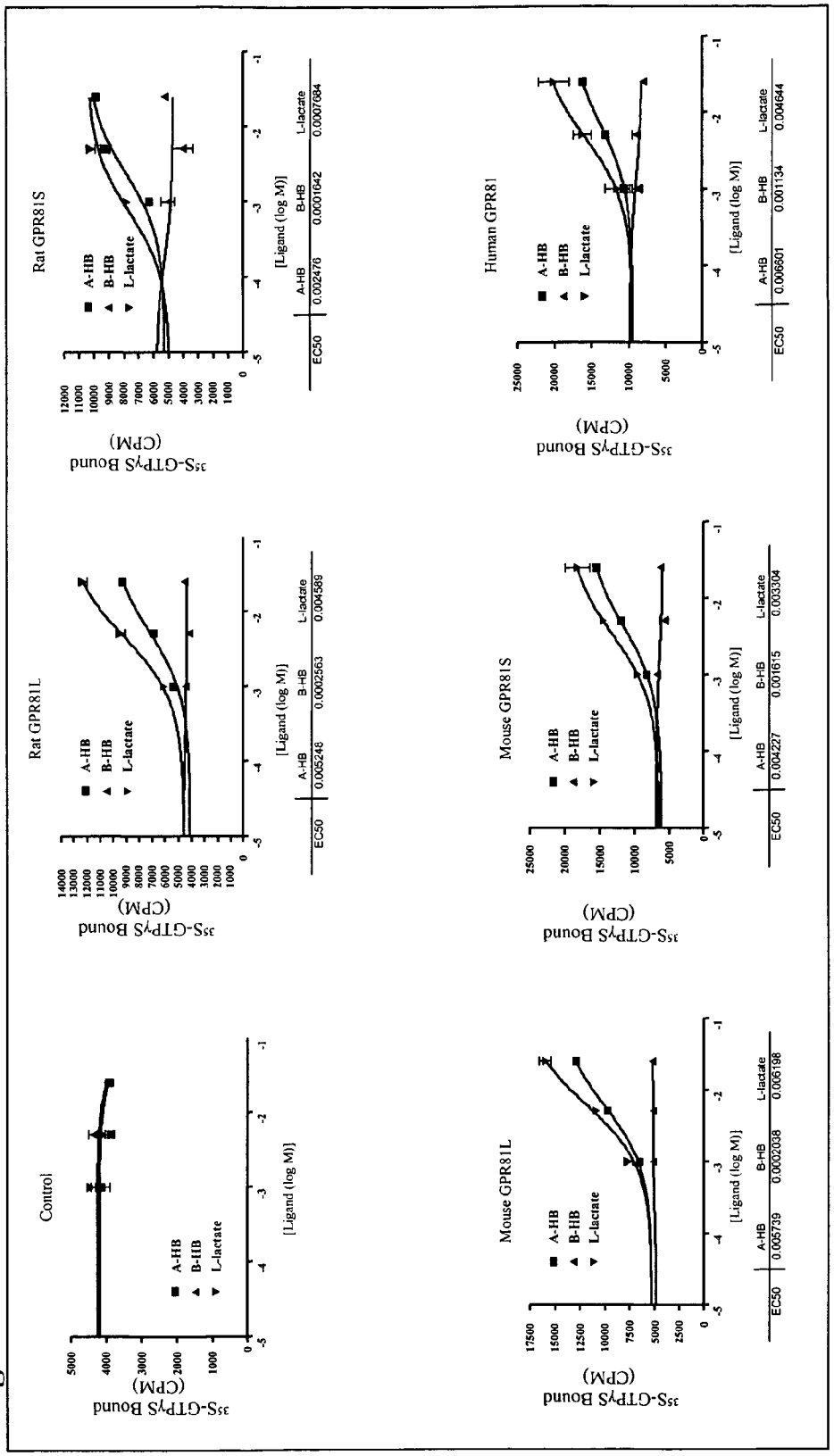
FIGS. 19 and 20 illustrate results from control cells and cells from different species expressing different forms of GPR81 tested with various concentration of L-lactate as the ligand (A-HB=α-hydroxybutyric acid; B-HB=β-hydroxybutyric acid).
Figure 20:
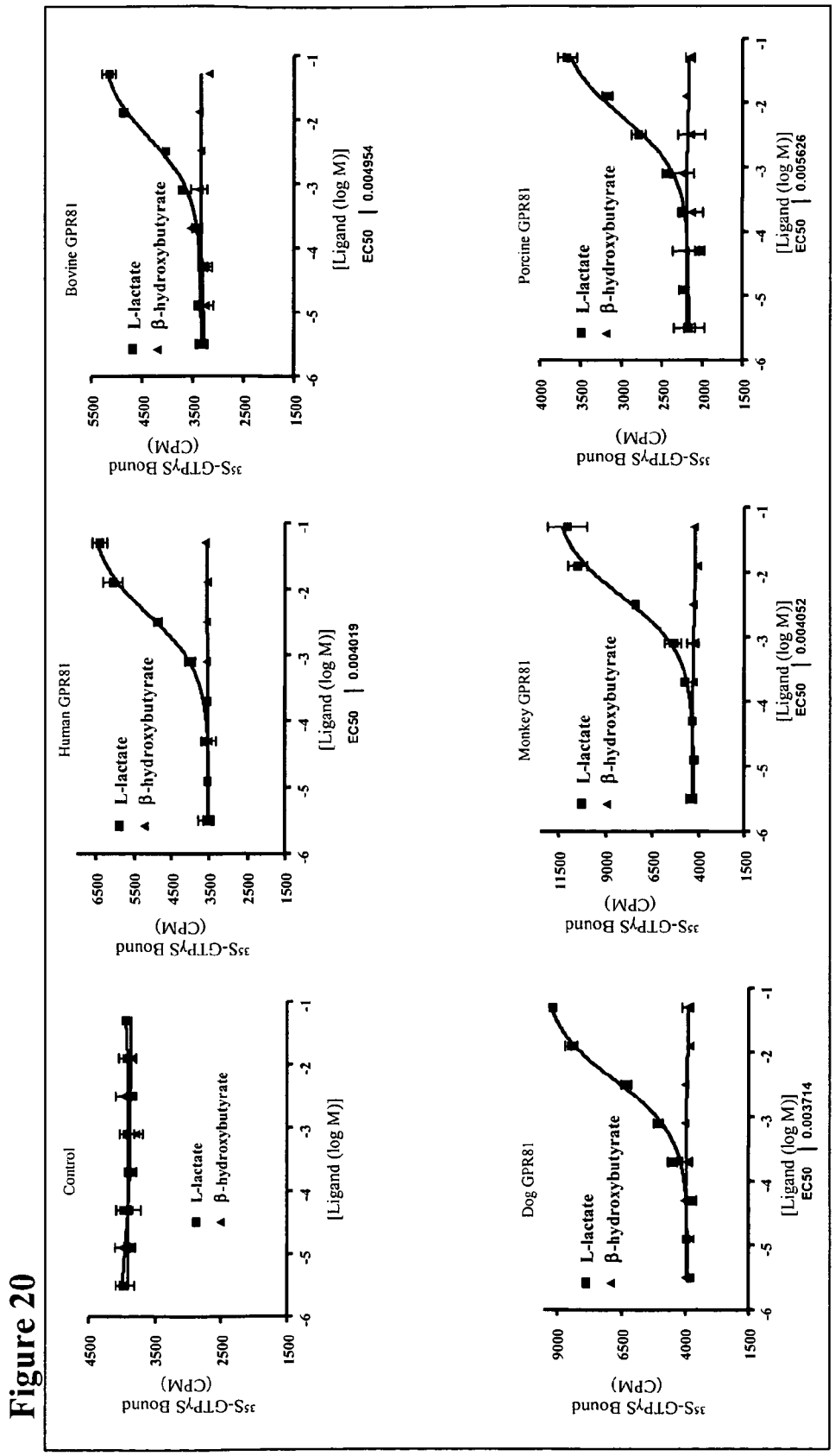

Both GPR81L and GPR81S from rat and mouse, as well as human GPR81, were each independently expressed in mammalian cells and used to assess L-lactate, α-hydroxybutyrate (A-HB), and β-hydroxybutyrate (B-HB) agonist ligand activity towards these GPR81 orthologs and isoforms via GTPγS binding assays, as described above. The results show that human GPR81 and GPR81L and GPR81S from both rat and mouse were activated by both L-lactate stimulation and A-HB stimulation at $EC_{50}$ values of from approximately 3 mM to approximately 6 mM, indicating that L-lactate and α-hydroxybutyrate serve as GPR81 agonist ligands (FIG. 19). B-HB did not activate any of the GPR81 forms tested (FIG. 19). A similar set of experiments were performed using human GPR81 and the bovine, dog, monkey, and porcine GPR81 cDNA-containing vectors and transfected cell lines described above. The results indicate, whereas B-HB did not activate any of human, bovine, dog, monkey, or porcine these GPR81 orthologs, L-lactate activated all of them at at $EC_{50}$ values of from approximately 3 mM to approximately 6 mM (FIG. 20). Collectively, these results indicate all of the GPR81 orthologs and isoforms tested are selectively activated by natural alpha hydroxyl acids, e.g., L-lactate and A-HB, and are not activated by beta hydroxyl acids, e.g., B-HB, or by nicotinic acid.

Pharmacological Characterization of GHB as an Agonist Ligand for GPR81.

Figure 21:
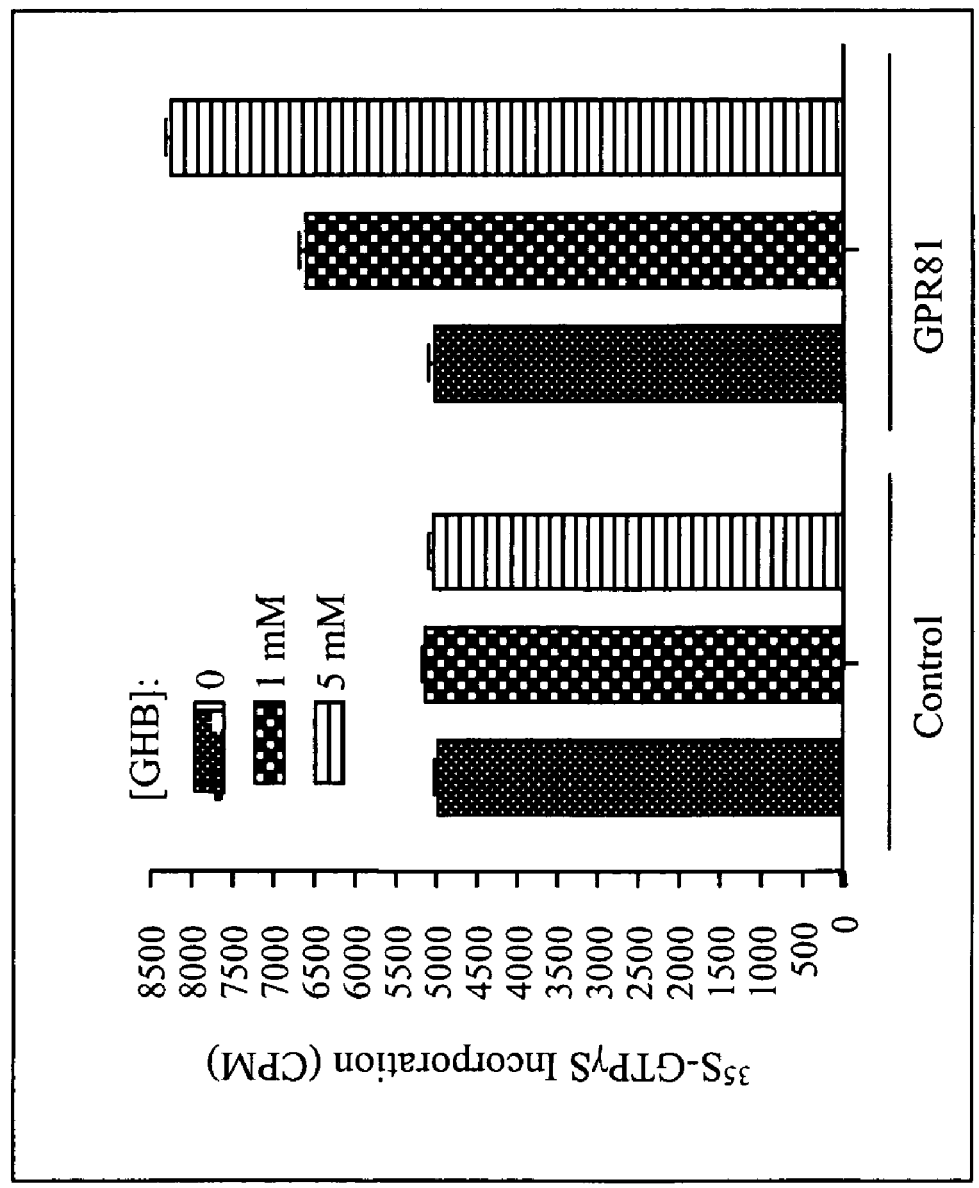
FIG. 21 depicts that GHB stimulates $^{35}$S-GTPγS binding in GPR81-expressing cells, but not in cells not expressing GPR81.

Different concentrations of GHB were tested for agonist ligand activity using GPR81-expressing cells or control cells not expressing a GPCR via GTPγS binding assays as described above. The results showed that GHB at 1 mM and 5 mM significantly stimulated $^{35}$S-GTPγS binding in GPR81-expressing cells but not in the control cells (FIG. 21), indicating that GHB is also an agonist ligand for GPR81. In the same experiment, γ-aminobutyrate did not stimulate $^{35}$S-GTPγS binding to GPR81-expressing cell membranes.

Pharmacological Characterization of Other Compounds as Agonist Ligands for GPR81.

Because L-Lactate, D-lactate, and GHB are each short chain organic hydroxyl acids, other chemically similar compounds were also tested for GPR81 ligand activity, including α-hydroxyacids, beta hydroxy acids, and gamma hydroxyl acids. The results are summarized in the table below.

TABLE 1

| Compound | GPR81 agonist activity |
| --- | --- |
| D-lactate | yes |
| α-hydroxybutyrate | yes |
| β-hydroxybutyrate | no |
| γ-hydroxybutyric acid (GHB) | yes |
| sodium hydroxyisobutyrate | yes |
| butyrate | no |
| glycolic acid, sodium salt | yes |
| glyoxylate | no |
| γ-aminobutyric acid (GABA) | no |
| L-amino acids | no |
| L-homoserine | no |
| pyruvate | no |
| acetate | no |
| formiate | no |
| glucose | no |
| dichloroacetate (DCA) | yes |
| trifluoroacetate (TFA) | yes |
| chlorodifluoroacetate (CDFA) | yes |
| 2-chloropropinoyl chloride | yes |
| 2-chloropropionic acid, sodium salt | yes |
| 2,2-dichloropropionic acid, sodium salt | no |
| tribromoacetate (TEA) | no |
| acetate | no |

In addition to L-lactate and α-hydroxybutyrate, the alpha-hydroxy acids D-lactate, hydroxy-iso-butyrate, and glycolate demonstrated significant GPR81 agonist activity. D-lactate, while also active or GPR81, was less efficacious as an agonist. Additionally, whereas neither acetate, pyruvate, formiate, nor glyoxylate activated GPR81, the halo-substituted organic acids dichloroactetate, difluoroacetate, trifluoroacetate, chlorodifluoroacetate, 2-chloropropinoyl chloride, and 2-chloropropinoate showed GPR81-agonist activity. Furthermore, whereas GHB activated GPR81, gamma-aminobutyric acid (GABA) did not activate it. Additionally, none of glucose, L-homoserine, or any L-amino acids tested activated GPR81. In addition, dichloroacetate (DCA), which is a compound used for the treatment of acidosis, and its related compounds were also tested as potential agonist for GPR81.

Although various aspects of the invention have been illustrated above by reference to examples and preferred embodiments, it will be appreciated that the scope of the invention is defined not by the foregoing description, but by the following claims properly construed under principles of patent law.

What is claimed is:

1. A method of identifying a test compound that binds to a GPR81 receptor, comprising the steps of: (a) contacting a receptor component with a test compound and with a reference compound, wherein said receptor component comprises a polypeptide having an amino acid sequence that is at least 80% homologous to human GPR81 of SEQ ID NO:32 and binds L-lactate, and said reference compound is L-lactate, D-lactate, α-hydroxybutyrate, γ-hydroxybutyrate, hydroxy-isobutyrate, glycolic acid, monochloroacetate, dichloroacetate, trifluoroacetate, chlorodifluoroacetate, 2-chloropropinoic acid, or 2-chloropropionic acid, or a salt thereof; (b) determining the amount of said reference compound that binds to said receptor component; and (c) comparing the amount determined in step (b) with a control measurement wherein said receptor component has been contacted with said reference compound in the absence of said test compound wherein an decrease in the amount of said reference compound that binds to said receptor component in the presence of said test compound compared with the amount of said reference compound that binds to said receptor component in the absence of said test compound indicates that the test compound binds to the GPCR81 receptor.

2. A method as defined in claim 1, wherein: said polypeptide of the receptor component comprises an amino acid sequence selected from the group consisting of SEQ ID NO:32, SEQ ID NO:34, SEQ ID NO:36, SEQ ID NO:38, SEQ ID NO:40, SEQ ID NO:42, SEQ ID NO:44, SEQ ID NO:46, and SEQ ID NO:48.

3. A method for of identifying a modulator of of a GPR81 receptor comprising: (a) contacting a test compound with an assay reagent comprising a receptor component having at least 80% homology to human GPR81 of SEQ ID NO:32 and that binds L-lactate; (b) determining a biological activity of said receptor component; and (c) comparing the result determined in step (b) with that of a control measurement wherein said receptor component is contacted with a ligand component selected from the group consisting of L-lactate, D-lactate, hydroxy-isobutyrate, glycolate, γ-hydroxybutyrate, monochioroacetate, dichloroactetate, difluoroacetate, trifluoroacetate, chlorodifluoroacetate, 2-chloropropinoate, 2,2-dichloropropinoate, and salts thereof in the absence of the test compound wherein a test compound that increases or decreases the biological activity of a GPR81 receptor is identified as a modulator of the GPR81 receptor.

4. A method as defined in claim 3, wherein said receptor component is a polypeptide comprising the amino acid sequence of SEQ ID NO:32, SEQ ID NO:34, SEQ ID NO:36, SEQ ID NO:38, SEQ ID NO:40, SEQ ID NO:42, SEQ ID NO:44, SEQ ID NO:46, or SEQ ID NO:48 expressed from the surface of a recombinant cell.

5. A method as defined in claim 3, wherein said receptor component is within an isolated cell membrane preparation.

* * * * *

SEQUENCE LISTING

<160> NUMBER OF SEQ ID NOS: 48

<210> SEQ ID NO 1
<211> LENGTH: 40
<212> TYPE: DNA
<213> ORGANISM: Artificial Sequence
<220> FEATURE:
<223> OTHER INFORMATION: Human GPR81 forward cloning primer

<400> SEQUENCE: 1
actggaattc gccaccatgt acaacgggtc gtgctgccgc                           40

<210> SEQ ID NO 2
<211> LENGTH: 40
<212> TYPE: DNA
<213> ORGANISM: Artificial Sequence
<220> FEATURE:
<223> OTHER INFORMATION: Human GPR81 reverse cloning primer

<400> SEQUENCE: 2
acgtcagcgg ccgctcagtg ccactcaaca atgtggggat                           40

<210> SEQ ID NO 3
<211> LENGTH: 45
<212> TYPE: DNA
<213> ORGANISM: Artificial Sequence
<220> FEATURE:
<223> OTHER INFORMATION: Mouse GPR81L forward cloning primer

<400> SEQUENCE: 3
agtcacgaat tcgccaccat gccagtcctc tctccaactg ctatg                     45

<210> SEQ ID NO 4
<211> LENGTH: 40
<212> TYPE: DNA
<213> ORGANISM: Artificial Sequence
<220> FEATURE:
<223> OTHER INFORMATION: Mouse GPR81L reverse cloning primer

<400> SEQUENCE: 4
acgtcagcgg ccgctcagtg ccactcaaca atgtggggat                        40

<210> SEQ ID NO 5
<211> LENGTH: 43
<212> TYPE: DNA
<213> ORGANISM: Artificial Sequence
<220> FEATURE:
<223> OTHER INFORMATION: Mouse GPR81S forward cloning primer

<400> SEQUENCE: 5
agtcacgaat tcgccaccat ggacaacggg tcgtgctgtc tca                    43

<210> SEQ ID NO 6
<211> LENGTH: 40
<212> TYPE: DNA
<213> ORGANISM: Artificial Sequence
<220> FEATURE:
<223> OTHER INFORMATION: Mouse GPR81S reverse cloning primer

<400> SEQUENCE: 6
acgtcagcgg ccgctcagtg ccactcaaca atgtggggat                        40

<210> SEQ ID NO 7
<211> LENGTH: 45
<212> TYPE: DNA
<213> ORGANISM: Artificial Sequence
<220> FEATURE:
<223> OTHER INFORMATION: Rat GPR81L forward cloning primer

<400> SEQUENCE: 7
agtcacgaat tcgccaccat gctcttcctc tctccgagtg ctatg                  45

<210> SEQ ID NO 8
<211> LENGTH: 38
<212> TYPE: DNA
<213> ORGANISM: Artificial Sequence
<220> FEATURE:
<223> OTHER INFORMATION: Rat GPR81L reverse cloning primer

<400> SEQUENCE: 8
actagagcgg ccgctcaaca cacttggaga ccccactg                          38

<210> SEQ ID NO 9
<211> LENGTH: 43
<212> TYPE: DNA
<213> ORGANISM: Artificial Sequence
<220> FEATURE:
<223> OTHER INFORMATION: Rat GPR81S forward cloning primer

<400> SEQUENCE: 9
agtcacgaat tcgccaccat ggacaacggg tcgtgctgtc tca                    43

<210> SEQ ID NO 10
<211> LENGTH: 38
<212> TYPE: DNA
<213> ORGANISM: Artificial Sequence
<220> FEATURE:
<223> OTHER INFORMATION: Rat GPR81S reverse cloning primer

<400> SEQUENCE: 10
actagagcgg ccgctcaaca cacttggaga ccccactg                          38

<210> SEQ ID NO 11
<211> LENGTH: 45
<212> TYPE: DNA
<213> ORGANISM: Artificial Sequence
<220> FEATURE:
<223> OTHER INFORMATION: Bovine GPR81S forward cloning primer

<400> SEQUENCE: 11
atgacagaat cgccaccat ggccaacagg tcgtgctgtc tcatc         45

<210> SEQ ID NO 12
<211> LENGTH: 41
<212> TYPE: DNA
<213> ORGANISM: Artificial Sequence
<220> FEATURE:
<223> OTHER INFORMATION: Bovine GPR81S reverse cloning primer

<400> SEQUENCE: 12
actagagcgg ccgccatgga gtatttctaa gtcaccaatc c         41

<210> SEQ ID NO 13
<211> LENGTH: 45
<212> TYPE: DNA
<213> ORGANISM: Artificial Sequence
<220> FEATURE:
<223> OTHER INFORMATION: Dog GPR81 forward cloning primer

<400> SEQUENCE: 13
actagagaat cgccaccat ggacaacggg tcgtgctgcc tcatc         45

<210> SEQ ID NO 14
<211> LENGTH: 40
<212> TYPE: DNA
<213> ORGANISM: Artificial Sequence
<220> FEATURE:
<223> OTHER INFORMATION: Dog GPR81 reverse cloning primer

<400> SEQUENCE: 14
actagagcgg ccgcgaggag gatacagctg aggaagggtg         40

<210> SEQ ID NO 15
<211> LENGTH: 44
<212> TYPE: DNA
<213> ORGANISM: Artificial Sequence
<220> FEATURE:
<223> OTHER INFORMATION: Monkey GPR81 forward cloning primer

<400> SEQUENCE: 15
actagagaat cgccaccat gtacaacggg tcgtgctgcc gcat         44

<210> SEQ ID NO 16
<211> LENGTH: 41
<212> TYPE: DNA
<213> ORGANISM: Artificial Sequence
<220> FEATURE:
<223> OTHER INFORMATION: Monkey GPR81 reverse cloning primer

<400> SEQUENCE: 16
atgatagcgg ccgctcagtg ccactcaaca gtgtgggat c         41

<210> SEQ ID NO 17
<211> LENGTH: 45
<212> TYPE: DNA
<213> ORGANISM: Artificial Sequence
<220> FEATURE:
<223> OTHER INFORMATION: Porcine GPR81 forward cloning primer

<400> SEQUENCE: 17
actgaggaat cgccaccat ggacaacggg tcatgctgcc tcatc         45

```
<210> SEQ ID NO 18
<211> LENGTH: 41
<212> TYPE: DNA
<213> ORGANISM: Artificial Sequence
<220> FEATURE:
<223> OTHER INFORMATION: Porcine GPR81 reverse cloning primer

<400> SEQUENCE: 18
actgaggcgg ccgctgtctg tccatcaatt ctgatgccat c                41

<210> SEQ ID NO 19
<211> LENGTH: 22
<212> TYPE: DNA
<213> ORGANISM: Artificial Sequence
<220> FEATURE:
<223> OTHER INFORMATION: Human GPR81 quantitative PCR forward primer

<400> SEQUENCE: 19
tgcccagcgt gtctgctaga ct                                     22

<210> SEQ ID NO 20
<211> LENGTH: 22
<212> TYPE: DNA
<213> ORGANISM: Artificial Sequence
<220> FEATURE:
<223> OTHER INFORMATION: Human GPR81 quantitative PCR reverse primer

<400> SEQUENCE: 20
tacaccaggg gatccagcat gc                                     22

<210> SEQ ID NO 21
<211> LENGTH: 24
<212> TYPE: DNA
<213> ORGANISM: Artificial Sequence
<220> FEATURE:
<223> OTHER INFORMATION: Rat GPR81 quantitative PCR forward primer

<400> SEQUENCE: 21
gagttgtttg gagcctgaga caga                                   24

<210> SEQ ID NO 22
<211> LENGTH: 21
<212> TYPE: DNA
<213> ORGANISM: Artificial Sequence
<220> FEATURE:
<223> OTHER INFORMATION: Rat GPR81 quantitative PCR reverse primer

<400> SEQUENCE: 22
ggggcttgag aagtagtaca c                                      21

<210> SEQ ID NO 23
<211> LENGTH: 22
<212> TYPE: DNA
<213> ORGANISM: Artificial Sequence
<220> FEATURE:
<223> OTHER INFORMATION: Mouse GPR81 quantitative PCR forward primer

<400> SEQUENCE: 23
ccggttcatc atggtggtgg ct                                     22

<210> SEQ ID NO 24
<211> LENGTH: 22
<212> TYPE: DNA
<213> ORGANISM: Artificial Sequence
<220> FEATURE:
<223> OTHER INFORMATION: Mouse GPR81 quantitative PCR reverse primer

<400> SEQUENCE: 24
```
ctcttctgac ctccgcgtct tc                                              22

<210> SEQ ID NO 25
<211> LENGTH: 22
<212> TYPE: DNA
<213> ORGANISM: Artificial Sequence
<220> FEATURE:
<223> OTHER INFORMATION: Human B-actin quantitative PCR forward primer

<400> SEQUENCE: 25
ggtcatcacc attggcaatg ag                                              22

<210> SEQ ID NO 26
<211> LENGTH: 22
<212> TYPE: DNA
<213> ORGANISM: Artificial Sequence
<220> FEATURE:
<223> OTHER INFORMATION: Human B-actin quantitative PCR reverse primer

<400> SEQUENCE: 26
gatcttgatc ttcattgtgc tg                                              22

<210> SEQ ID NO 27
<211> LENGTH: 20
<212> TYPE: DNA
<213> ORGANISM: Artificial Sequence
<220> FEATURE:
<223> OTHER INFORMATION: Rat B-actin quantitative PCR forward primer

<400> SEQUENCE: 27
caacacagtg ctgtctggtg                                                 20

<210> SEQ ID NO 28
<211> LENGTH: 19
<212> TYPE: DNA
<213> ORGANISM: Artificial Sequence
<220> FEATURE:
<223> OTHER INFORMATION: Rat B-actin quantitative PCR reverse primer

<400> SEQUENCE: 28
gatccacatc tgctggaag                                                  19

<210> SEQ ID NO 29
<211> LENGTH: 21
<212> TYPE: DNA
<213> ORGANISM: Artificial Sequence
<220> FEATURE:
<223> OTHER INFORMATION: Mouse B-actin quantitative PCR forward primer

<400> SEQUENCE: 29
acaacggctc cggcatgtgc a                                               21

<210> SEQ ID NO 30
<211> LENGTH: 22
<212> TYPE: DNA
<213> ORGANISM: Artificial Sequence
<220> FEATURE:
<223> OTHER INFORMATION: Mouse B-actin quantitative PCR reverse primer

<400> SEQUENCE: 30
gtgtggtgcc agatcttctc ca                                              22

<210> SEQ ID NO 31
<211> LENGTH: 1041
<212> TYPE: DNA
<213> ORGANISM: Homo Sapiens

<400> SEQUENCE: 31

```
atgtacaacg ggtcgtgctg ccgcatcgag ggggacacca tctcccaggt gatgccgccg      60
ctgctcattg tggcctttgt gctgggcgca ctaggcaatg gggtcgccct gtgtggtttc     120
tgcttccaca tgaagacctg gaagcccagc actgtttacc tttcaatttt ggccgtggct     180
gatttcctcc ttatgatctg cctgccttt cggacagact attacctcag acgtagacac      240
tgggcttttg gggacattcc ctgccgagtg gggctcttca cgttggccat gaacagggcc     300
gggagcatcg tgttccttac ggtggtggct gcggacaggt atttcaaagt ggtccacccc     360
caccacgcgg tgaacactat ctccacccgg gtggcggctg gcatcgtctg caccctgtgg     420
gccctggtca tcctgggaac agtgtatctt ttgctggaga accatctctg cgtgcaagag     480
acggccgtct cctgtgagag cttcatcatg gagtcggcca atggctggca tgacatcatg     540
ttccagctgg agttctttat gcccctcggc atcatcttat tttgctcctt caagattgtt     600
tggagcctga ggcggaggca gcagctggcc agacaggctc ggatgaagaa ggcgacccgg     660
ttcatcatgg tggtggcaat tgtgttcatc acatgctacc tgcccagcgt gtctgctaga     720
ctctatttcc tctggacggt gccctcgagt gcctgcgatc cctctgtcca tggggccctg     780
cacataaccc tcagcttcac ctacatgaac agcatgctgg atccctggt gtattatttt     840
tcaagcccct cctttcccaa attctacaac aagctcaaaa tctgcagtct gaaacccaag     900
cagccaggac actcaaaaac acaaaggccg aagagatgc caatttcgaa cctcggtcgc     960
aggagttgca tcagtgtggc aaatagttc caaagccagt ctgatgggca atgggatccc    1020
cacattgttg agtggcactg a                                             1041
```

<210> SEQ ID NO 32
<211> LENGTH: 346
<212> TYPE: PRT
<213> ORGANISM: Homo Sapiens

<400> SEQUENCE: 32

```
Met Tyr Asn Gly Ser Cys Cys Arg Ile Glu Gly Asp Thr Ile Ser Gln
1               5                   10                  15

Val Met Pro Pro Leu Leu Ile Val Ala Phe Val Leu Gly Ala Leu Gly
            20                  25                  30

Asn Gly Val Ala Leu Cys Gly Phe Cys Phe His Met Lys Thr Trp Lys
        35                  40                  45

Pro Ser Thr Val Tyr Leu Phe Asn Leu Ala Val Ala Asp Phe Leu Leu
    50                  55                  60

Met Ile Cys Leu Pro Phe Arg Thr Asp Tyr Tyr Leu Arg Arg His
65                  70                  75                  80

Trp Ala Phe Gly Asp Ile Pro Cys Arg Val Gly Leu Phe Thr Leu Ala
                85                  90                  95

Met Asn Arg Ala Gly Ser Ile Val Phe Leu Thr Val Val Ala Ala Asp
            100                 105                 110

Arg Tyr Phe Lys Val Val His Pro His Ala Val Asn Thr Ile Ser
        115                 120                 125

Thr Arg Val Ala Ala Gly Ile Val Cys Thr Leu Trp Ala Leu Val Ile
    130                 135                 140

Leu Gly Thr Val Tyr Leu Leu Leu Glu Asn His Leu Cys Val Gln Glu
145                 150                 155                 160

Thr Ala Val Ser Cys Glu Ser Phe Ile Met Glu Ser Ala Asn Gly Trp
                165                 170                 175
```

His Asp Ile Met Phe Gln Leu Glu Phe Phe Met Pro Leu Gly Ile Ile
            180                 185                 190

Leu Phe Cys Ser Phe Lys Ile Val Trp Ser Leu Arg Arg Gln Gln
        195                 200                 205

Leu Ala Arg Gln Ala Arg Met Lys Lys Ala Thr Arg Phe Ile Met Val
210                 215                 220

Val Ala Ile Val Phe Ile Thr Cys Tyr Leu Pro Ser Val Ser Ala Arg
225                 230                 235                 240

Leu Tyr Phe Leu Trp Thr Val Pro Ser Ser Ala Cys Asp Pro Ser Val
                245                 250                 255

His Gly Ala Leu His Ile Thr Leu Ser Phe Thr Tyr Met Asn Ser Met
            260                 265                 270

Leu Asp Pro Leu Val Tyr Tyr Phe Ser Ser Pro Ser Phe Pro Lys Phe
        275                 280                 285

Tyr Asn Lys Leu Lys Ile Cys Ser Leu Lys Pro Lys Gln Pro Gly His
    290                 295                 300

Ser Lys Thr Gln Arg Pro Glu Glu Met Pro Ile Ser Asn Leu Gly Arg
305                 310                 315                 320

Arg Ser Cys Ile Ser Val Ala Asn Ser Phe Gln Ser Gln Ser Asp Gly
                325                 330                 335

Gln Trp Asp Pro His Ile Val Glu Trp His
            340                 345

<210> SEQ ID NO 33
<211> LENGTH: 1056
<212> TYPE: DNA
<213> ORGANISM: Rattus sp.

<400> SEQUENCE: 33
atgctcttcc tctctccgag tgctatggac aacgggtcgt gctgtctcat cgaggggggaa      60 cccatcaccc aggtaatgcc acctttactc atcctggcct cctgcttgg agccctgggc       120 aacggcctag ccctgtgtgg tttctgcttt cacatgaaga cctggaagtc gagcactatt      180
taccttttca acttggctgt agccgatttt ctcctcatga tctgcctacc ccttcggaca      240
gactactacc tcagacgtag gcattggatt ttgggggata ttccctgccg cctggtcctc      300
ttcatgctgg ccatgaatag ggccggaagc attgtcttcc tcactgtggt ggccgtggac      360
aggtatttca aagtggtcca cccccaccat atggtgaacg ccatctccaa tcggactgca      420
gctgccatcg tctgtgtcct ctggactttg gtcatcttgg ggactgtgta tcttctgatg      480
gagagtcacc tgtgtgtgcg ggggatggtg tcatcttgtg agagcttcat catggagtca      540
gccaacgggt ggcacgatat catgttccag ctggagttct cctgcccccct gaccatcatc     600 ttgttctgct ccttcagagt tgtttggagc ctgagacaga ggcaacagct gaccagacag      660
gctcggatga ggagggccac ccggttcatc atggtggtgg cttccgtgtt catcacgtgt      720
tacctgccca gcgtgttggc gaggctctac ttcctctgga cggtgccctc cagtgcctgt      780 gaccccctctg tccacatagc tctccatgtc accctgagtc tcacctacct gaacagcatg     840 ctggacccctc ttgtgtacta cttctcaagc ccctcgttcc ccaaattcta tgccaagctc     900
aaaatccgca gcttgaaacc cagacgccca ggacgctcgc aggcacggag gtcggaagag      960
atgccaattt cgaatctctg tcgtaagagt tccaccgatg tggtaaatag ttcccagagg     1020
ccgtctgacg ggcagtgggg tctccaagtg tgttga                             1056

<210> SEQ ID NO 34
<211> LENGTH: 351

<212> TYPE: PRT
<213> ORGANISM: Rattus sp.

<400> SEQUENCE: 34

```
Met Leu Phe Leu Ser Pro Ser Ala Met Asp Asn Gly Ser Cys Cys Leu
1               5                   10                  15
Ile Glu Gly Glu Pro Ile Thr Gln Val Met Pro Pro Leu Leu Ile Leu
                20                  25                  30
Ala Phe Leu Leu Gly Ala Leu Gly Asn Gly Leu Ala Leu Cys Gly Phe
            35                  40                  45
Cys Phe His Met Lys Thr Trp Lys Ser Ser Thr Ile Tyr Leu Phe Asn
        50                  55                  60
Leu Ala Val Ala Asp Phe Leu Leu Met Ile Cys Leu Pro Leu Arg Thr
65                  70                  75                  80
Asp Tyr Tyr Leu Arg Arg Arg His Trp Ile Leu Gly Asp Ile Pro Cys
                85                  90                  95
Arg Leu Val Leu Phe Met Leu Ala Met Asn Arg Ala Gly Ser Ile Val
            100                 105                 110
Phe Leu Thr Val Val Ala Val Asp Arg Tyr Phe Lys Val Val His Pro
        115                 120                 125
His His Met Val Asn Ala Ile Ser Asn Arg Thr Ala Ala Ala Ile Val
130                 135                 140
Cys Val Leu Trp Thr Leu Val Ile Leu Gly Thr Val Tyr Leu Leu Met
145                 150                 155                 160
Glu Ser His Leu Cys Val Arg Gly Met Val Ser Ser Cys Glu Ser Phe
                165                 170                 175
Ile Met Glu Ser Ala Asn Gly Trp His Asp Ile Met Phe Gln Leu Glu
            180                 185                 190
Phe Phe Leu Pro Leu Thr Ile Ile Leu Phe Cys Ser Phe Arg Val Val
        195                 200                 205
Trp Ser Leu Arg Gln Arg Gln Leu Thr Arg Gln Ala Arg Met Arg
    210                 215                 220
Arg Ala Thr Arg Phe Ile Met Val Val Ala Ser Val Phe Ile Thr Cys
225                 230                 235                 240
Tyr Leu Pro Ser Val Leu Ala Arg Leu Tyr Phe Leu Trp Thr Val Pro
                245                 250                 255
Ser Ser Ala Cys Asp Pro Ser Val His Ile Ala Leu His Val Thr Leu
            260                 265                 270
Ser Leu Thr Tyr Leu Asn Ser Met Leu Asp Pro Leu Val Tyr Tyr Phe
        275                 280                 285
Ser Ser Pro Ser Phe Pro Lys Phe Tyr Ala Lys Leu Lys Ile Arg Ser
290                 295                 300
Leu Lys Pro Arg Arg Pro Gly Arg Ser Gln Ala Arg Arg Ser Glu Glu
305                 310                 315                 320
Met Pro Ile Ser Asn Leu Cys Arg Lys Ser Ser Thr Asp Val Val Asn
                325                 330                 335
Ser Ser Gln Arg Pro Ser Asp Gly Gln Trp Gly Leu Gln Val Cys
            340                 345                 350
```

<210> SEQ ID NO 35
<211> LENGTH: 1056
<212> TYPE: DNA
<213> ORGANISM: Mus musculus

<400> SEQUENCE: 35

```
atgccagtcc tctctccaac tgctatggac aacgggtcgt gctgtctcat cgaggggag    60
```

```
cccatctccc aagtgatgcc tcctctactc atcctggtct tcgtgcttgg cgccctgggc    120
aacggcatag ccctgtgcgg cttctgcttt cacatgaaga cctggaagtc aagcactatt    180
tacctttcca acttggctgt ggccgatttt ctcctcatga tctgcttacc ccttcggaca    240
gactactacc tcagacgcag acactggatt tttggagata tcgcctgtcg cctggtcctc    300
ttcaagctgg ccatgaatag ggccgggagc attgtcttcc tcactgtggt ggctgtggat    360
aggtatttca aagtggtcca ccccaccat atggtgaatg ccatctccaa ccggactgcc    420
gccgccaccg cctgtgtcct ctggactttg tcatcttgg ggactgtgta tcttctgatg    480
gagagtcacc tgtgtgtgca ggggacactg tcgtcctgtg agagcttcat catggagtca    540
gccaacgggt ggcacgatgt catgttccag ctggagttct tcctgcccct gacaatcatc    600
ttgttctgct cggtcaacgt tgtttggagc ctgagacgga ggcagcagct gaccagacag    660
gctcggatga ggagggccac ccggttcatc atggtggtgg cttctgtgtt catcacgtgt    720
tacctgccca gcgtgctggc taggctctac ttcctctgga cggtgcccac tagtgcctgt    780 gaccccctctg tccacacagc cctccacgtc accctgagct tcacctacct gaacagtatg    840
ctggatcccc ttgtatatta cttctcaagc ccctcgctcc ccaaattcta caccaagctc    900
acaatctgca gcctgaagcc caaacgccca ggacgcacga agacgcggag gtcagaagag    960
atgccaattt cgaacctctg cagtaagagc tccatcgatg gggcaaatcg ttcccagagg   1020
ccatctgacg ggcagtggga tctccaagtg tgttga                             1056
```

<210> SEQ ID NO 36
<211> LENGTH: 351
<212> TYPE: PRT
<213> ORGANISM: Mus musculus

<400> SEQUENCE: 36

```
Met Pro Val Leu Ser Pro Thr Ala Met Asp Asn Gly Ser Cys Cys Leu
1               5                   10                  15

Ile Glu Gly Glu Pro Ile Ser Gln Val Met Pro Pro Leu Leu Ile Leu
            20                  25                  30

Val Phe Val Leu Gly Ala Leu Gly Asn Gly Ile Ala Leu Cys Gly Phe
        35                  40                  45

Cys Phe His Met Lys Thr Trp Lys Ser Ser Thr Ile Tyr Leu Phe Asn
    50                  55                  60

Leu Ala Val Ala Asp Phe Leu Leu Met Ile Cys Leu Pro Leu Arg Thr
65                  70                  75                  80

Asp Tyr Tyr Leu Arg Arg Arg His Trp Ile Phe Gly Asp Ile Ala Cys
                85                  90                  95

Arg Leu Val Leu Phe Lys Leu Ala Met Asn Arg Ala Gly Ser Ile Val
            100                 105                 110

Phe Leu Thr Val Val Ala Val Asp Arg Tyr Phe Lys Val Val His Pro
        115                 120                 125

His His Met Val Asn Ala Ile Ser Asn Arg Thr Ala Ala Ala Thr Ala
    130                 135                 140

Cys Val Leu Trp Thr Leu Val Ile Leu Gly Thr Val Tyr Leu Leu Met
145                 150                 155                 160

Glu Ser His Leu Cys Val Gln Gly Thr Leu Ser Ser Cys Glu Ser Phe
                165                 170                 175

Ile Met Glu Ser Ala Asn Gly Trp His Asp Val Met Phe Gln Leu Glu
            180                 185                 190

Phe Phe Leu Pro Leu Thr Ile Ile Leu Phe Cys Ser Val Asn Val Val
```

|   |   | 195 |   |   | 200 |   |   |   | 205 |   |   |
|---|---|---|---|---|---|---|---|---|---|---|---|

Trp Ser Leu Arg Arg Arg Gln Gln Leu Thr Arg Gln Ala Arg Met Arg
210                     215                     220

Arg Ala Thr Arg Phe Ile Met Val Val Ala Ser Val Phe Ile Thr Cys
225                     230                     235                     240

Tyr Leu Pro Ser Val Leu Ala Arg Leu Tyr Phe Leu Trp Thr Val Pro
                245                     250                     255

Thr Ser Ala Cys Asp Pro Ser Val His Thr Ala Leu His Val Thr Leu
                260                     265                     270

Ser Phe Thr Tyr Leu Asn Ser Met Leu Asp Pro Leu Val Tyr Tyr Phe
            275                     280                     285

Ser Ser Pro Ser Leu Pro Lys Phe Tyr Thr Lys Leu Thr Ile Cys Ser
290                     295                     300

Leu Lys Pro Lys Arg Pro Gly Arg Thr Lys Thr Arg Arg Ser Glu Glu
305                     310                     315                     320

Met Pro Ile Ser Asn Leu Cys Ser Lys Ser Ile Asp Gly Ala Asn
                325                     330                     335

Arg Ser Gln Arg Pro Ser Asp Gly Gln Trp Asp Leu Gln Val Cys
            340                     345                     350

<210> SEQ ID NO 37
<211> LENGTH: 1032
<212> TYPE: DNA
<213> ORGANISM: Rattus sp.

<400> SEQUENCE: 37

```
atggacaacg ggtcgtgctg tctcatcgag ggggaaccca tcacccaggt aatgccacct      60
ttactcatcc tggccttcct gcttggagcc ctgggcaacg cctagccct gtgtggtttc      120
tgctttcaca tgaagacctg gaagtcgagc actatttacc ttttcaactt ggctgtagcc      180
gattttctcc tcatgatctg cctacccctt cggacagact actacctcag acgtaggcat      240
tggattttgg gggatattcc ctgccgcctg gtcctcttca tgctggccat gaatagggcc      300
ggaagcattg tcttcctcac tgtggtggcc gtggacaggt atttcaaagt ggtccacccc      360
caccatatgg tgaacgccat ctccaatcgg actgcagctg ccatcgtctg tgtcctctgg      420
actttggtca tcttggggac tgtgtatctt ctgatggaga tcacctgtg tgtgcgggg      480
atggtgtcat cttgtgagag cttcatcatg gagtcagcca acgggtggca cgatatcatg      540
ttccagctgg agttcttcct gcccctgacc atcatcttgt tctgctcctt cagagttgtt      600
tggagcctga cagaggca acagctgacc agacaggctc ggatgaggag ggccacccgg      660
ttcatcatgg tggtggcttc cgtgttcatc acgtgttacc tgcccagcgt gttggcgagg      720
ctctacttcc tctggacggt gccctccagt gcctgtgacc cctctgtcca catagctctc      780
catgtcaccc tgagtctcac ctacctgaac agcatgctgg accctcttgt gtactacttc      840
tcaagcccct cgttccccaa attctatgcc aagctcaaaa tccgcagctt gaaacccaga      900
cgcccaggac gctcgcaggc acggaggtcg gaagagatgc caatttcgaa tctctgtcgt      960
aagagttcca ccgatgtggt aaatagttcc cagaggccgt ctgacgggca gtggggtctc      1020
caagtgtgtt ga                                                          1032
```

<210> SEQ ID NO 38
<211> LENGTH: 343
<212> TYPE: PRT
<213> ORGANISM: Rattus sp.

<400> SEQUENCE: 38

| | | | | | | | | | | | |
|---|---|---|---|---|---|---|---|---|---|---|---|
Met | Asp | Asn | Gly | Ser | Cys | Cys | Leu | Ile | Glu | Gly | Glu | Pro | Ile | Thr | Gln
1 | | | | 5 | | | | | 10 | | | | | 15

Val Met Pro Pro Leu Leu Ile Leu Ala Phe Leu Leu Gly Ala Leu Gly
            20                  25                  30

Asn Gly Leu Ala Leu Cys Gly Phe Cys Phe His Met Lys Thr Trp Lys
        35                  40                  45

Ser Ser Thr Ile Tyr Leu Phe Asn Leu Ala Val Ala Asp Phe Leu Leu
    50                  55                  60

Met Ile Cys Leu Pro Leu Arg Thr Asp Tyr Tyr Leu Arg Arg Arg His
65                  70                  75                  80

Trp Ile Leu Gly Asp Ile Pro Cys Arg Leu Val Leu Phe Met Leu Ala
                85                  90                  95

Met Asn Arg Ala Gly Ser Ile Val Phe Leu Thr Val Val Ala Val Asp
            100                 105                 110

Arg Tyr Phe Lys Val Val His Pro His His Met Val Asn Ala Ile Ser
        115                 120                 125

Asn Arg Thr Ala Ala Ala Ile Val Cys Val Leu Trp Thr Leu Val Ile
    130                 135                 140

Leu Gly Thr Val Tyr Leu Leu Met Glu Ser His Leu Cys Val Arg Gly
145                 150                 155                 160

Met Val Ser Ser Cys Glu Ser Phe Ile Met Glu Ser Ala Asn Gly Trp
                165                 170                 175

His Asp Ile Met Phe Gln Leu Glu Phe Phe Leu Pro Leu Thr Ile Ile
            180                 185                 190

Leu Phe Cys Ser Phe Arg Val Val Trp Ser Leu Arg Gln Arg Gln Gln
        195                 200                 205

Leu Thr Arg Gln Ala Arg Met Arg Arg Ala Thr Arg Phe Ile Met Val
    210                 215                 220

Val Ala Ser Val Phe Ile Thr Cys Tyr Leu Pro Ser Val Leu Ala Arg
225                 230                 235                 240

Leu Tyr Phe Leu Trp Thr Val Pro Ser Ser Ala Cys Asp Pro Ser Val
                245                 250                 255

His Ile Ala Leu His Val Thr Leu Ser Leu Thr Tyr Leu Asn Ser Met
            260                 265                 270

Leu Asp Pro Leu Val Tyr Tyr Phe Ser Ser Pro Ser Phe Pro Lys Phe
        275                 280                 285

Tyr Ala Lys Leu Lys Ile Arg Ser Leu Lys Pro Arg Arg Pro Gly Arg
    290                 295                 300

Ser Gln Ala Arg Arg Ser Glu Glu Met Pro Ile Ser Asn Leu Cys Arg
305                 310                 315                 320

Lys Ser Ser Thr Asp Val Val Asn Ser Ser Gln Arg Pro Ser Asp Gly
                325                 330                 335

Gln Trp Gly Leu Gln Val Cys
                340

<210> SEQ ID NO 39
<211> LENGTH: 1032
<212> TYPE: DNA
<213> ORGANISM: Mus musculus

<400> SEQUENCE: 39
atggacaacg ggtcgtgctg tctcatcgag ggggagccca ctcccaagt gatgcctcct    60 ctactcatcc tggtcttcgt gcttggcgcc ctgggcaacg gcatagccct gtgcggcttc   120
tgctttcaca tgaagacctg gaagtcaagc actatttacc ttttcaactt ggctgtggcc   180

```
gattttctcc tcatgatctg cttacccctt cggacagact actacctcag acgcagacac    240
tggatttttg agatatcgc ctgtcgcctg gtcctcttca agctggccat gaatagggcc    300
gggagcattg tcttcctcac tgtggtggct gtggataggt atttcaaagt ggtccacccc    360
caccatatgg tgaatgccat ctccaaccgg actgccgccg ccaccgcctg tgtcctctgg    420
actttggtca tcttggggac tgtgtatctt ctgatggaga gtcacctgtg tgtgcagggg    480
acactgtcgt cctgtgagag cttcatcatg gagtcagcca acgggtggca cgatgtcatg    540
ttccagctgg agttcttcct gcccctgaca atcatcttgt tctgctcggt caacgttgtt    600
tggagcctga gacggaggca gcagctgacc agacaggctc ggatgaggag ggccacccgg    660
ttcatcatgg tggtggcttc tgtgttcatc acgtgttacc tgcccagcgt gctggctagg    720
ctctacttcc tctggacggt gcccactagt gcctgtgacc cctctgtcca cacagccctc    780
cacgtcaccc tgagcttcac ctacctgaac agtatgctgg atcccctcgt atattacttc    840
tcaagcccct cgctccccaa attctacacc aagctcacaa tctgcagcct gaagcccaaa    900
cgcccaggac gcacgaagac gcggaggtca gaagagatgc caatttcgaa cctctgcagt    960
aagagctcca tcgatggggc aaatcgttcc cagaggccat tgacgggca gtgggatctc    1020 caagtgtgtt ga                                                        1032

<210> SEQ ID NO 40
<211> LENGTH: 343
<212> TYPE: PRT
<213> ORGANISM: Mus musculus

<400> SEQUENCE: 40

Met Asp Asn Gly Ser Cys Cys Leu Ile Glu Gly Glu Pro Ile Ser Gln
1               5                   10                  15

Val Met Pro Pro Leu Leu Ile Leu Val Phe Val Leu Gly Ala Leu Gly
                20                  25                  30

Asn Gly Ile Ala Leu Cys Gly Phe Cys Phe His Met Lys Thr Trp Lys
            35                  40                  45

Ser Ser Thr Ile Tyr Leu Phe Asn Leu Ala Val Ala Asp Phe Leu Leu
        50                  55                  60

Met Ile Cys Leu Pro Leu Arg Thr Asp Tyr Tyr Leu Arg Arg His
65                  70                  75                  80

Trp Ile Phe Gly Asp Ile Ala Cys Arg Leu Val Leu Phe Lys Leu Ala
                85                  90                  95

Met Asn Arg Ala Gly Ser Ile Val Phe Leu Thr Val Ala Val Asp
                100                 105                 110

Arg Tyr Phe Lys Val Val His Pro His His Met Val Asn Ala Ile Ser
                115                 120                 125

Asn Arg Thr Ala Ala Thr Ala Cys Val Leu Trp Thr Leu Val Ile
            130                 135                 140

Leu Gly Thr Val Tyr Leu Leu Met Glu Ser His Leu Cys Val Gln Gly
145                 150                 155                 160

Thr Leu Ser Ser Cys Glu Ser Phe Ile Met Glu Ser Ala Asn Gly Trp
                165                 170                 175

His Asp Val Met Phe Gln Leu Glu Phe Phe Leu Pro Leu Thr Ile Ile
                180                 185                 190

Leu Phe Cys Ser Val Asn Val Val Trp Ser Leu Arg Arg Arg Gln Gln
            195                 200                 205

Leu Thr Arg Gln Ala Arg Met Arg Arg Ala Thr Arg Phe Ile Met Val
        210                 215                 220
```

Val Ala Ser Val Phe Ile Thr Cys Tyr Leu Pro Ser Val Leu Ala Arg
225                 230                 235                 240

Leu Tyr Phe Leu Trp Thr Val Pro Thr Ser Ala Cys Asp Pro Ser Val
            245                 250                 255

His Thr Ala Leu His Val Thr Leu Ser Phe Thr Tyr Leu Asn Ser Met
            260                 265                 270

Leu Asp Pro Leu Val Tyr Tyr Phe Ser Ser Pro Ser Leu Pro Lys Phe
        275                 280                 285

Tyr Thr Lys Leu Thr Ile Cys Ser Leu Lys Pro Lys Arg Pro Gly Arg
    290                 295                 300

Thr Lys Thr Arg Arg Ser Glu Glu Met Pro Ile Ser Asn Leu Cys Ser
305                 310                 315                 320

Lys Ser Ser Ile Asp Gly Ala Asn Arg Ser Gln Arg Pro Ser Asp Gly
                325                 330                 335

Gln Trp Asp Leu Gln Val Cys
            340

<210> SEQ ID NO 41
<211> LENGTH: 1008
<212> TYPE: DNA
<213> ORGANISM: Bos taurus

<400> SEQUENCE: 41
atggccaaca ggtcgtgctg tctcatccag gggtaccaca tgcccgaggt gatgccgtcg      60
ctgctaatcc tcgcctttgt gctcggcatc ctgggcaacg gcgtcgccct ctgtggtttc     120
tgctttcaca tgaagacctg gaagccgagc actatttacc tgttcaactt ggccgtggcc     180
gacttccttc tgatgatctg cctgcccttt cggacagact actacctcag acagaggcaa     240
tgggcgtttg aggatattcc ttgtcgggtg gtgctcttca tgctggccat gaacagggcg     300
gggagcattg tcttcctcac agtggtggct gtggaccggt attttaaagt ggtccacccc     360
caccacatgg tgaacaccat ctccaactgg actgcggttg gcattgtctg tgtcctttgg     420
accctggtca tcttggggac tctgtatctt ctgttggaga accatctgtg tgtgcaagag     480
aagatcatag cttgtgagag cttcatcatg gtatcggcca atggctggca tgatgtcatg     540
ttccagctgg agttctttct gcccttggc atcatcttgt tctgctcctt caagatcatt     600
tggagcctca gcagaggca gcgtctggcc aggcagagcc ggatgaagaa gcctgttcgt     660
ttcatcatga tggtggcggt ggtgtttatt gcctgctacc tgcccagcgc gttggccaga     720
ctgtatttcc tctggacggt gcctccagc gcctgcaatc catctgtcca tgtggccctc     780
cacgtcaccc tcagcttcac ctacataaac agcatgctgg accccctggt atattatttt     840
tcaagtccct cattccccaa attctacacc aagctcaaaa tctgcagtgt gagacctagg     900
tgtccgggat gcttcaagag gccagagggg atgcccactt ccaacctttg ttgcaagagt     960
tgcatcagtg ttgcaaatag cttccaaagc cagtctgagg ggcagtga              1008

<210> SEQ ID NO 42
<211> LENGTH: 335
<212> TYPE: PRT
<213> ORGANISM: Bos taurus

<400> SEQUENCE: 42

Met Ala Asn Arg Ser Cys Cys Leu Ile Gln Gly Tyr His Met Pro Glu
1               5                   10                  15

Val Met Pro Ser Leu Leu Ile Leu Ala Phe Val Leu Gly Ile Leu Gly
            20                  25                  30

Asn Gly Val Ala Leu Cys Gly Phe Cys Phe His Met Lys Thr Trp Lys
            35                  40                  45

Pro Ser Thr Ile Tyr Leu Phe Asn Leu Ala Val Ala Asp Phe Leu Leu
 50                  55                  60

Met Ile Cys Leu Pro Phe Arg Thr Asp Tyr Tyr Leu Arg Gln Arg Gln
 65                  70                  75                  80

Trp Ala Phe Glu Asp Ile Pro Cys Arg Val Val Leu Phe Met Leu Ala
                 85                  90                  95

Met Asn Arg Ala Gly Ser Ile Val Phe Leu Thr Val Val Ala Val Asp
            100                 105                 110

Arg Tyr Phe Lys Val Val His Pro His His Met Val Asn Thr Ile Ser
        115                 120                 125

Asn Trp Thr Ala Val Gly Ile Val Cys Val Leu Trp Thr Leu Val Ile
    130                 135                 140

Leu Gly Thr Leu Tyr Leu Leu Glu Asn His Leu Cys Val Gln Glu
145                 150                 155                 160

Lys Ile Ile Ala Cys Glu Ser Phe Ile Met Val Ser Ala Asn Gly Trp
                165                 170                 175

His Asp Val Met Phe Gln Leu Glu Phe Phe Leu Pro Leu Gly Ile Ile
            180                 185                 190

Leu Phe Cys Ser Phe Lys Ile Ile Trp Ser Leu Lys Gln Arg Gln Arg
        195                 200                 205

Leu Ala Arg Gln Ser Arg Met Lys Lys Pro Val Arg Phe Ile Met Met
    210                 215                 220

Val Ala Val Val Phe Ile Ala Cys Tyr Leu Pro Ser Ala Leu Ala Arg
225                 230                 235                 240

Leu Tyr Phe Leu Trp Thr Val Pro Ser Ser Ala Cys Asn Pro Ser Val
                245                 250                 255

His Val Ala Leu His Val Thr Leu Ser Phe Thr Tyr Ile Asn Ser Met
            260                 265                 270

Leu Asp Pro Leu Val Tyr Tyr Phe Ser Ser Pro Ser Phe Pro Lys Phe
        275                 280                 285

Tyr Thr Lys Leu Lys Ile Cys Ser Val Arg Pro Arg Cys Pro Gly Cys
    290                 295                 300

Phe Lys Arg Pro Glu Gly Met Pro Thr Ser Asn Leu Cys Cys Lys Ser
305                 310                 315                 320

Cys Ile Ser Val Ala Asn Ser Phe Gln Ser Gln Ser Glu Gly Gln
                325                 330                 335

<210> SEQ ID NO 43
<211> LENGTH: 1089
<212> TYPE: DNA
<213> ORGANISM: Canis sp.

<400> SEQUENCE: 43
atggacaacg ggtcgtgctg cctcatcgag ggggacccca tctctcaggt gatgccaccg      60
ctgctgatcc tggccttcgt gctgggcgca ctgggcaatg catggccct ctgtggtttc     120 tgcttttaca tgaagacctg gaagccgagc actatttacc tttttaacct ggccgtggcc     180
gacttccttc tcatgatctg cctgcccttc cggacagact actactggag acacaggcaa     240
tgggcctttg aggacattcc gtgtcgggtg gcgctcttca tgctggccat gaacagggct     300
gggagcatca tcttcctcac tgtggtggcg gtggacaggt acttcaaagt ggtccacccc     360
caccacgtgc tgaacaccat ttccaaccgg actgcagctg gcatcgtctg tgcccttggg     420

```
atcatggtca tcctgggcac tctctacctt ttgatggaga accatctgtg cgtgcatgag    480
aagaccatat cttgtgagag cttcatcatg gagtcagcca atggctggca cgacatcatg    540
ttccagctgg aattcttcct ccctctcggc atcatcctgt tctgctcctt caggattatt    600
tggagtctga agcagaggcg gcagctggcc aggcagactc ggatgaagaa ggctacccgg    660
ttcatcatgg ttgtggcggt tgtgttcatc acgtgctacc tgcccagcgt gtcggccaga    720
ctctatttcc tctggacggt gccctcgagt gcctgcgacc cctctgtcca cgtagccctc    780
cacatcaccc tcagcttcac ctacatgaac agcatgctgg atcctctggt gtattatttt    840
tcgagtcctg tattccccaa attctacacc aagctcaaga tccgcggttt gcgaccaaag    900
agtccagggc actccaagac ccagaggccg gaagagatgc aatcccaaa gctctgtcgc     960 aagagttgtg tccgtgtggc aagcagcttc cagagccaat ccaacgagca gcaggatctt   1020
caaatgtgtg gaatggcact gaaacaggca gacaggcaaa acccaaggag gacagacaaa   1080
cagacttag                                                           1089
```

<210> SEQ ID NO 44
<211> LENGTH: 362
<212> TYPE: PRT
<213> ORGANISM: Canis sp.

<400> SEQUENCE: 44

```
Met Asp Asn Gly Ser Cys Cys Leu Ile Glu Gly Asp Pro Ile Ser Gln
1               5                   10                  15

Val Met Pro Pro Leu Leu Ile Leu Ala Phe Val Leu Gly Ala Leu Gly
                20                  25                  30

Asn Gly Met Ala Leu Cys Gly Phe Cys Phe Tyr Met Lys Thr Trp Lys
            35                  40                  45

Pro Ser Thr Ile Tyr Leu Phe Asn Leu Ala Val Ala Asp Phe Leu Leu
        50                  55                  60

Met Ile Cys Leu Pro Phe Arg Thr Asp Tyr Tyr Trp Arg His Arg Gln
65                  70                  75                  80

Trp Ala Phe Glu Asp Ile Pro Cys Arg Val Ala Leu Phe Met Leu Ala
                85                  90                  95

Met Asn Arg Ala Gly Ser Ile Ile Phe Leu Thr Val Ala Val Asp
            100                 105                 110

Arg Tyr Phe Lys Val Val His Pro His His Val Leu Asn Thr Ile Ser
        115                 120                 125

Asn Arg Thr Ala Ala Gly Ile Val Cys Ala Leu Trp Ile Met Val Ile
    130                 135                 140

Leu Gly Thr Leu Tyr Leu Leu Met Glu Asn His Leu Cys Val His Glu
145                 150                 155                 160

Lys Thr Ile Ser Cys Glu Ser Phe Ile Met Glu Ser Ala Asn Gly Trp
                165                 170                 175

His Asp Ile Met Phe Gln Leu Glu Phe Phe Leu Pro Leu Gly Ile Ile
            180                 185                 190

Leu Phe Cys Ser Phe Arg Ile Ile Trp Ser Leu Lys Gln Arg Arg Gln
        195                 200                 205

Leu Ala Arg Gln Thr Arg Met Lys Lys Ala Thr Arg Phe Ile Met Val
    210                 215                 220

Val Ala Val Val Phe Ile Thr Cys Tyr Leu Pro Ser Val Ser Ala Arg
225                 230                 235                 240

Leu Tyr Phe Leu Trp Thr Val Pro Ser Ser Ala Cys Asp Pro Ser Val
                245                 250                 255
```

```
His Val Ala Leu His Ile Thr Leu Ser Phe Thr Tyr Met Asn Ser Met
            260                 265                 270

Leu Asp Pro Leu Val Tyr Tyr Phe Ser Ser Pro Val Phe Pro Lys Phe
            275                 280                 285

Tyr Thr Lys Leu Lys Ile Arg Gly Leu Arg Pro Lys Ser Pro Gly His
            290                 295                 300

Ser Lys Thr Gln Arg Pro Glu Glu Met Pro Ile Pro Lys Leu Cys Arg
305                 310                 315                 320

Lys Ser Cys Val Arg Val Ala Ser Ser Phe Gln Ser Gln Ser Asn Glu
                325                 330                 335

Gln Gln Asp Leu Gln Met Cys Gly Met Ala Leu Lys Gln Ala Asp Arg
            340                 345                 350

Gln Asn Pro Arg Arg Thr Asp Lys Gln Thr
            355                 360
```

<210> SEQ ID NO 45
<211> LENGTH: 1014
<212> TYPE: DNA
<213> ORGANISM: Macaca mulatta

<400> SEQUENCE: 45

```
atgtacaacg gtcgtgctg ccgcatcgag ggggacacca tctcccaggt gatgccgccg      60
ctgctcattg tggcctttgt gctgggcgca ctaggcaatg gggtcgccct gtgtggtttc    120
tgcttccaca tgaagaccctg gaagccaagc actgtttacc ttttcaactt ggccgtggct    180
gatttcctcc ttatgatctg cctgccttttt cggacagact attacctcag acgtagacac    240
tgggcttttg gggacattcc ctgccgggtg gggctcttca ccttggccat gaacagggcc    300
gggagcatcg tgttccttac ggtggtggct gtggacaggt atttcaaagt ggtccacccc    360
caccacgcgg tgaacaccat ctccaaccgg acggcagctg gcatcgtctg caccctgtgg    420
accctggtca tcctgggaac actgtatctt ttgctggaga accatctctg tgtgcaagag    480
acggctgtct cctgtgagag cttcatcatg gagtcggcca atggctggca tgacatcatg    540
ttccagctgg agttctttct gcccctcggc atcatcttat tttgctcctt caagattgtt    600
tggagcctga ggcggaggca gcagctggcc agacaggctc ggatgaagaa ggcgacccgg    660
ttcatcatgg tggtggcagt tgtgttcatc acgtgctacc tgcccagcgt gtccgccaga    720
ctctatttcc tctggacggt gcctcgagt gcctgcgatc cctctgtcca tgtggccctg    780
cacatcaccc tcagcttcac ctacatgaac agcatgctgg atccctggt gtattatttt    840
tcaagcccct cgtttcccaa attctacaac aagctcaaaa tctgcagtct gaaacccaag    900
cagccaggac actcaaaaac acaaaggccg aagagatgc caatttcgaa cctcagtcgc    960
aagagttgcc tcagtgtgac aactagttcc caaagccagt ctgatgggca gtag          1014
```

<210> SEQ ID NO 46
<211> LENGTH: 337
<212> TYPE: PRT
<213> ORGANISM: Macaca mulatta

<400> SEQUENCE: 46

```
Met Tyr Asn Gly Ser Cys Cys Arg Ile Glu Gly Asp Thr Ile Ser Gln
1               5                   10                  15

Val Met Pro Pro Leu Leu Ile Val Ala Phe Val Leu Gly Ala Leu Gly
            20                  25                  30

Asn Gly Val Ala Leu Cys Gly Phe Cys Phe His Met Lys Thr Trp Lys
            35                  40                  45
```

```
Pro Ser Thr Val Tyr Leu Phe Asn Leu Ala Val Ala Asp Phe Leu Leu
     50                  55                  60

Met Ile Cys Leu Pro Phe Arg Thr Asp Tyr Tyr Leu Arg Arg Arg His
 65                  70                  75                  80

Trp Ala Phe Gly Asp Ile Pro Cys Arg Val Gly Leu Phe Thr Leu Ala
                 85                  90                  95

Met Asn Arg Ala Gly Ser Ile Val Phe Leu Thr Val Val Ala Val Asp
            100                 105                 110

Arg Tyr Phe Lys Val Val His Pro His Ala Val Asn Thr Ile Ser
            115                 120                 125

Asn Arg Thr Ala Ala Gly Ile Val Cys Thr Leu Trp Thr Leu Val Ile
130                 135                 140

Leu Gly Thr Leu Tyr Leu Leu Leu Glu Asn His Leu Cys Val Gln Glu
145                 150                 155                 160

Thr Ala Val Ser Cys Glu Ser Phe Ile Met Glu Ser Ala Asn Gly Trp
                165                 170                 175

His Asp Ile Met Phe Gln Leu Glu Phe Phe Leu Pro Leu Gly Ile Ile
            180                 185                 190

Leu Phe Cys Ser Phe Lys Ile Val Trp Ser Leu Arg Arg Arg Gln Gln
            195                 200                 205

Leu Ala Arg Gln Ala Arg Met Lys Lys Ala Thr Arg Phe Ile Met Val
210                 215                 220

Val Ala Val Phe Ile Thr Cys Tyr Leu Pro Ser Val Ser Ala Arg
225                 230                 235                 240

Leu Tyr Phe Leu Trp Thr Val Pro Ser Ser Ala Cys Asp Pro Ser Val
                245                 250                 255

His Val Ala Leu His Ile Thr Leu Ser Phe Thr Tyr Met Asn Ser Met
            260                 265                 270

Leu Asp Pro Leu Val Tyr Tyr Phe Ser Ser Pro Ser Phe Pro Lys Phe
            275                 280                 285

Tyr Asn Lys Leu Lys Ile Cys Ser Leu Lys Pro Lys Gln Pro Gly His
            290                 295                 300

Ser Lys Thr Gln Arg Pro Gln Glu Met Pro Ile Ser Asn Leu Ser Arg
305                 310                 315                 320

Lys Ser Cys Leu Ser Val Thr Thr Ser Ser Gln Ser Gln Ser Asp Gly
                325                 330                 335

Gln

<210> SEQ ID NO 47
<211> LENGTH: 1023
<212> TYPE: DNA
<213> ORGANISM: Sus sp.

<400> SEQUENCE: 47
atggacaacg ggtcatgctg cctcatccag ggggacccta tctcccaggc gatgccgccg      60
ctgctgatcc tggccttcgt gctcggtgcc ctgggcaacg tatcgccct gtgtggattt     120 tgctttcaca tgaagacctg gaagcccagc actatttacc ttttcaactt ggctgtggct     180
gactttcttc tcatgatctg cctgcccttt cggacggact attaccgcag acacaggcaa     240
tgggcctttg gggatattcc ctgtcgagcg gtgctcttca tgctggccat gaacagggcc     300
gggagcattg tcttccttac ggtggtggct gtggacaggt attttaaagt ggtccacccc     360
caccatatgg tgaatgccat ctccaaccgg accgcaattg gcatcgtctg cgcccttttgg   420 accatggtca tcgtggggac tctgtatctt ttgatggaga accatctgtg tgtgcaagag     480
```

```
aagaccatag cttgtgagag cttcatcatg gagtcagcca atggctggca tgacgtcatg      540
ttccagctgg agttcttcct gccccttggc atcatcttgt tctgctcctt caaggtcatt      600
tggagcctgg agcagaggca gcacctggcc aggcaggctc ggatgaagag ggctacacgg      660
ttcatcgtgt tggtggcagt tgtgttcatc acgggctacc tgcctagcgt gtcagccaga      720
ctgtatttcc tctggacggt gccctccagc gtctgtgacc cctctgtgca tgtagccctc      780
catgtcaccc tcagcttcac ctacatgaac agcatgctgg atcccctggt gtattatttt      840
tcaagtccct cgttccccaa attctactcc aagctcaaaa tctgcagctt gagacctaag      900
catccaggac gctccaagag gccagaagag atgccaattt caaacctttg tcacaagagt      960
tgcattagtg tggcaaatag cttccaaagt caatcagatg tgcagtggga tccccagatg     1020
tga                                                                   1023
```

<210> SEQ ID NO 48
<211> LENGTH: 340
<212> TYPE: PRT
<213> ORGANISM: Sus sp.

<400> SEQUENCE: 48

```
Met Asp Asn Gly Ser Cys Cys Leu Ile Gln Gly Asp Pro Ile Ser Gln
 1               5                  10                  15

Ala Met Pro Pro Leu Leu Ile Leu Ala Phe Val Leu Gly Ala Leu Gly
                20                  25                  30

Asn Gly Ile Ala Leu Cys Gly Phe Cys Phe His Met Lys Thr Trp Lys
            35                  40                  45

Pro Ser Thr Ile Tyr Leu Phe Asn Leu Ala Val Ala Asp Phe Leu Leu
        50                  55                  60

Met Ile Cys Leu Pro Phe Arg Thr Asp Tyr Tyr Arg Arg His Arg Gln
 65                  70                  75                  80

Trp Ala Phe Gly Asp Ile Pro Cys Arg Ala Val Leu Phe Met Leu Ala
                 85                  90                  95

Met Asn Arg Ala Gly Ser Ile Val Phe Leu Thr Val Val Ala Val Asp
            100                 105                 110

Arg Tyr Phe Lys Val Val His Pro His His Met Val Asn Ala Ile Ser
        115                 120                 125

Asn Arg Thr Ala Ile Gly Ile Val Cys Ala Leu Trp Thr Met Val Ile
    130                 135                 140

Val Gly Thr Leu Tyr Leu Leu Met Glu Asn His Leu Cys Val Gln Glu
145                 150                 155                 160

Lys Thr Ile Ala Cys Glu Ser Phe Ile Met Glu Ser Ala Asn Gly Trp
                165                 170                 175

His Asp Val Met Phe Gln Leu Glu Phe Phe Leu Pro Leu Gly Ile Ile
            180                 185                 190

Leu Phe Cys Ser Phe Lys Val Ile Trp Ser Leu Glu Gln Arg Gln His
        195                 200                 205

Leu Ala Arg Gln Ala Arg Met Lys Arg Ala Thr Arg Phe Ile Val Val
    210                 215                 220

Val Ala Val Val Phe Ile Thr Gly Tyr Leu Pro Ser Val Ser Ala Arg
225                 230                 235                 240

Leu Tyr Phe Leu Trp Thr Val Pro Ser Ser Val Cys Asp Pro Ser Val
                245                 250                 255

His Val Ala Leu His Val Thr Leu Ser Phe Thr Tyr Met Asn Ser Met
            260                 265                 270

Leu Asp Pro Leu Val Tyr Tyr Phe Ser Ser Pro Ser Phe Pro Lys Phe
```

```
                          275                     280                     285
      Tyr Ser Lys Leu Lys Ile Cys Ser Leu Arg Pro Lys His Pro Gly Arg
          290                     295                     300

Ser Lys Arg Pro Glu Glu Met Pro Ile Ser Asn Leu Cys His Lys Ser
      305                     310                     315                 320

Cys Ile Ser Val Ala Asn Ser Phe Gln Ser Gln Ser Asp Val Gln Trp
                      325                     330                     335

Asp Pro Gln Met
                  340
```